US010150948B2

(12) United States Patent
Stahl et al.

(10) Patent No.: US 10,150,948 B2
(45) Date of Patent: Dec. 11, 2018

(54) COMPOSITIONS AND METHODS FOR PRODUCING AND ADMINISTERING BROWN ADIPOCYTES

(71) Applicant: The Regents of the University of California, Oakland, CA (US)

(72) Inventors: Andreas Stahl, Oakland, CA (US);
Kevin Tharp, Oakland, CA (US);
Kevin E. Healy, Oakland, CA (US);
Amit Kumar Jha, Oakland, CA (US);
Judith Kraiczy, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 197 days.

(21) Appl. No.: 15/036,297

(22) PCT Filed: Dec. 10, 2014

(86) PCT No.: PCT/US2014/069612
§ 371 (c)(1),
(2) Date: May 12, 2016

(87) PCT Pub. No.: WO2015/089228
PCT Pub. Date: Jun. 18, 2015

(65) Prior Publication Data
US 2016/0298085 A1      Oct. 13, 2016

Related U.S. Application Data

(60) Provisional application No. 61/914,672, filed on Dec. 11, 2013.

(51) Int. Cl.
| | |
|---|---|
| *A61K 35/35* | (2015.01) |
| *C12N 5/0775* | (2010.01) |
| *C12N 5/077* | (2010.01) |
| *A61K 9/00* | (2006.01) |
| *C12N 11/04* | (2006.01) |

(52) U.S. Cl.
CPC .......... *C12N 5/0653* (2013.01); *A61K 9/0024* (2013.01); *A61K 35/35* (2013.01); *C12N 11/04* (2013.01); *C12N 2501/734* (2013.01); *C12N 2506/1384* (2013.01); *C12N 2533/80* (2013.01)

(58) Field of Classification Search
CPC .................. C12N 5/0653; C12N 11/04; C12N 2506/1384; A61K 9/0024; A61K 35/35
See application file for complete search history.

(56) References Cited

U.S. PATENT DOCUMENTS

| | | | |
|---|---|---|---|
| 8,354,274 B2 | 1/2013 | Fadeev et al. | |
| 9,683,213 B2* | 6/2017 | Murphy | C12N 5/0606 |
| 2007/0026518 A1 | 2/2007 | Healy et al. | |
| 2011/0104113 A1 | 5/2011 | Sugita et al. | |
| 2012/0321671 A1 | 12/2012 | Boyden et al. | |
| 2013/0115673 A1 | 5/2013 | West | |

FOREIGN PATENT DOCUMENTS

| | | |
|---|---|---|
| EP | 1178834 | 2/2002 |
| JP | 2011-195568 A | 10/2011 |
| WO | WO 2011/115420 A2 | 9/2011 |
| WO | WO 2013/082106 | 6/2013 |

OTHER PUBLICATIONS

Wagner et al., Comparative characteristics of mesenchymal stem cells from human bone marrow, adipose tissue, and umbilical cord blood. Experimental Hematology, vol. 33 (2005) pp. 1402-1416.*
R. Ian Freshney, "Quantitation." In: Culture of Animal Cell: A Manual of Basic Technique and Specialized Applications. (Hoboken, NJ, John Wiley & Sons, Inc., 2010), pp. 163-186. QH585.2.F74 2010.*
Ahfeldt et al.; "Programming human pluripotent stem cells into white and brown adipocytes"; Nat Cell Biol. Jan. 15, 2012; 14(2): 202-19.
Cannon, et al.; "Brown adipose tissue: function and physiological significance"; Physiol Rev. Jan. 2004; 84(1): 277-359.
Cypess, et al.; "Identification and importance of brown adipose tissue in adult humans"; N Engl J Med. Apr. 9, 2009; 360(15): 1509-17.
Elabd et al.; "Human multipotent adipose-derived stem cells differentiate into functional brown adipocytes"; Stem Cells. Nov. 2009; 27(11): 2753-60.
Ghorbani et al.; "Hypertrophy of brown adipocytes in brown and white adipose tissues and reversal of diet-induced obesity in rats treated with a beta3-adrenoceptor agonist"; Biochem Pharmacol. Jul. 1, 1997; 54(1): 121-31.
Nishio et al.; "Production of functional classical brown adipocytes from human pluripotent stem cells using specific hemopoietin cocktail without gene transfer"; Stem Cells. Nov. 2009; 27(11): 2753-60.
Ohno et al.; "PPARy agonists induce a white-to-brown fat conversion through stabilization of PRDM16 protein"; Cell Metab. Sep. 5, 2012; 16(3): 394-406.
Ouellet et al.; "Brown adipose tissue oxidative metabolism contributes to energy expenditure during acute cold exposure in humans"; J Clin Endocrinol Metab. Jan. 2011; 96(1): 192-9.
Rodeheffer et al.; "Identification of white adipocyte progenitor cells in vivo"; Cell. Oct. 17, 2008; 135(2): 240-9.
Schulz et al.; "Identification of inducible brown adipocyte progenitors residing in skeletal muscle and white fat"; Proc Natl Acad Sci U S A. Jan. 4, 2011; 108(1): 143-8.

(Continued)

*Primary Examiner* — Kara D Johnson
(74) *Attorney, Agent, or Firm* — Bozicevic Field & Francis, LLP; Paula A. Borden

(57) ABSTRACT

The present disclosure provides compositions comprising a hydrogel and a cell adhesion ligand that enhances the differentiation of mesenchymal stem cells into brown adipocytes, and/or enhances the maintenance of brown adipocytes. In some cases, a subject composition includes cells that are embedded within the hydrogel. The present disclosure also provides methods of making and using the subject compositions.

26 Claims, 5 Drawing Sheets
Specification includes a Sequence Listing.

(56) References Cited

OTHER PUBLICATIONS

Stanford et al.; "Brown adipose tissue regulates glucose homeostasis and insulin sensitivity"; J Clin Invest. Jan. 2, 2013; 123(1): 215-23.
Tseng et al.: "New role of bone morphogenetic protein 7 in brown adipogenesis and energy expenditure"; Nature. Aug. 21, 2008; 454(7207): 1000-4.
Van Marken Lichtenbelt et al.; "Cold-Activated Brown Adipose Tissue in Healthy Men"; N Engl J Med. Apr. 9, 2009; 360(15): 1500-8.
Virtanen et al.; "Functional Brown Adipose Tissue in Healthy Adults"; N Engl J Med. Apr. 9, 2009; 360(15): 1518-25.
Huang, et al.; "Adipose-Derived Stem Cells: Isolation, Characterization, and Differentiation Potential"; Cell Transplantation; vol. 22, pp. 701-709 (2013).
Jha, et al.; "Controlling the adhesion and differentiation of mesenchymal stem cells using hyaluronic acid-based, doubly crosslinked networks"; Biomaterials; vol. 32, pp. 2466-2478 (2011).
Jha, et al.; "Structural Analysis and Mechanical Characterization of Hyaluronic Acid-Based Doubly Cross-Linked Networks"; Macromolecules; vol. 42, No. 2, pp. 537-546 (2009).
Schmidt, et al.; "Effect of avidin-like proteins and biotin modification on mesenchymal stem cell adhesion"; Biomaterials; vol. 34, pp. 3758-3762 (2013).
Tharp, et al.; "Matrix-Assisted Transplantation of Functional Beige Adipose Tissue"; Diabetes; vol. 64, pp. 3713-3724 (Nov. 2015).
Wilson, et al.; "Arrays of topographically and peptide-functionalized hydrogels for analysis of biomimetic extracellular matrix properties"; J. Vac. Sci. Technol. B.; vol. 30, No. 6, 7 pages (Nov. 1, 2012).
Xu, et al.; "Hyaluronic Acid-Based Hydrogels: from a Natural Polysaccharide to Complex Networks"; Soft Matter; vol. 8, No. 12, pp. 3280-3294 (2012).
Yamada, et al.; "Laminin-111-derived peptide-hyaluronate hydrogels as a synthetic basement membrane"; Biomaterials; vol. 34, pp. 6539-6547 (2013).
Yamada, et al.; "Peptide-hyaluronate Hydrogels as a Three-dimensional Cell Culture Matrix"; Peptide Science; pp. 59-62 (Jan. 1, 2013).
Barczyk, et al.; "Integrins"; Cell Tissue Res.; vol. 339, pp. 269-280 (2010).
Kato, et al.; "Cell Surface Syndecan-1 on Distinct Cell Types Differs in Fine Structure and Ligand Binding of Its Heparan Sulfate Chains"; The Journal of Biological Chemistry; vol. 269, Issue of Jul. 22, pp. 1881-18890 (1994).

\* cited by examiner

```
SEQUENCE LISTING

<160> NUMBER OF SEQ ID NOS: 45

<210> SEQ ID NO 1
<211> LENGTH: 12
<212> TYPE: PRT
<213> ORGANISM: Artificial sequence
<220> FEATURE:
<223> OTHER INFORMATION: Synthetic amino acid seqeunce

<400> SEQUENCE: 1

Arg Lys Arg Leu Gln Val Gln Leu Ser Ile Arg Thr
1               5                   10

<210> SEQ ID NO 2
<211> LENGTH: 12
<212> TYPE: PRT
<213> ORGANISM: Artificial sequence
<220> FEATURE:
<223> OTHER INFORMATION: Synthetic amino acid seqeunce

<400> SEQUENCE: 2

Lys Ala Phe Asp Ile Thr Tyr Val Arg Leu Lys Phe
1               5                   10

<210> SEQ ID NO 3
<211> LENGTH: 12
<212> TYPE: PRT
<213> ORGANISM: Artificial sequence
<220> FEATURE:
<223> OTHER INFORMATION: Synthetic amino acid seqeunce

<400> SEQUENCE: 3

Thr Trp Tyr Lys Ile Ala Phe Gln Arg Asn Arg Lys
1               5                   10

<210> SEQ ID NO 4
<211> LENGTH: 12
<212> TYPE: PRT
<213> ORGANISM: Artificial sequence
<220> FEATURE:
<223> OTHER INFORMATION: Synthetic amino acid seqeunce

<400> SEQUENCE: 4

Asn Gly Glu Pro Arg Gly Asp Thr Tyr Arg Ala Tyr
1               5                   10
```

<210> SEQ ID NO 5
<211> LENGTH: 12
<212> TYPE: PRT
<213> ORGANISM: Artificial sequence
<220> FEATURE:
<223> OTHER INFORMATION: Synthetic amino acid seqeunce

<400> SEQUENCE: 5

Asn Arg Trp His Ser Ile Tyr Ile Thr Arg Phe Gly
1               5                   10

<210> SEQ ID NO 6
<211> LENGTH: 8
<212> TYPE: PRT
<213> ORGANISM: Artificial sequence
<220> FEATURE:
<223> OTHER INFORMATION: Synthetic amino acid seqeunce

<400> SEQUENCE: 6

Glu Ile Leu Asp Val Pro Ser Thr
1               5

<210> SEQ ID NO 7
<211> LENGTH: 15
<212> TYPE: PRT
<213> ORGANISM: Artificial sequence
<220> FEATURE:
<223> OTHER INFORMATION: Synthetic amino acid seqeunce

<400> SEQUENCE: 7

Val Ser Trp Phe Ser Arg His Arg Tyr Ser Pro Phe Ala Val Ser
1               5                   10                  15

<210> SEQ ID NO 8
<211> LENGTH: 15
<212> TYPE: PRT
<213> ORGANISM: Artificial sequence
<220> FEATURE:
<223> OTHER INFORMATION: Synthetic amino acid seqeunce

<400> SEQUENCE: 8

Cys Gly Gly Arg Lys Arg Leu Gln Val Gln Leu Ser Ile Arg Thr
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Synthetic amino acid seqeunce

<400> SEQUENCE: 9

Cys Gly Gly Lys Ala Phe Asp Ile Thr Tyr Val Arg Leu Lys Phe
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: Synthetic amino acid seqeunce

<400> SEQUENCE: 10

Cys Gly Gly Thr Trp Tyr Lys Ile Ala Phe Gln Arg Asn Arg Lys
1               5                   10                  15

```
<210> SEQ ID NO 11
<211> LENGTH: 15
<212> TYPE: PRT
<213> ORGANISM: Artificial sequence
<220> FEATURE:
<223> OTHER INFORMATION: Synthetic amino acid seqeunce

<400> SEQUENCE: 11

Cys Gly Gly Asn Gly Glu Pro Arg Gly Asp Thr Tyr Arg Ala Tyr
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: Synthetic amino acid seqeunce

<400> SEQUENCE: 12

Cys Gly Gly Asn Arg Trp His Ser Ile Tyr Ile Thr Arg Phe Gly
1               5                   10                  15

<210> SEQ ID NO 13
<211> LENGTH: 11
<212> TYPE: PRT
<213> ORGANISM: Artificial sequence
<220> FEATURE:
<223> OTHER INFORMATION: Synthetic amino acid seqeunce

<400> SEQUENCE: 13

Cys Gly Gly Glu Ile Leu Asp Val Pro Ser Thr
1               5                   10

<210> SEQ ID NO 14
<211> LENGTH: 18
<212> TYPE: PRT
<213> ORGANISM: Artificial sequence
<220> FEATURE:
<223> OTHER INFORMATION: Synthetic amino acid seqeunce

<400> SEQUENCE: 14

Cys Gly Gly Val Ser Trp Phe Ser Arg His Arg Tyr Ser Pro Phe Ala
1               5                   10                  15

Val Ser

<210> SEQ ID NO 15
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa is L or Q

<400> SEQUENCE: 15

Pro Xaa Gly Met Thr Ser
1               5

<210> SEQ ID NO 16
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
```

```
<222> LOCATION: (2)..(2)
<223> OTHER INFORMATION: Xaa is L or Q

<400> SEQUENCE: 16

Pro Xaa Gly Met Thr
1               5

<210> SEQ ID NO 17
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 17

Cys Gly Leu Val Pro Ala Gly Ser Gly Pro
1               5                  10

<210> SEQ ID NO 18
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 18

Ser Leu Leu Lys Ser Arg Met Val Pro Asn Phe Asn
1               5                  10

<210> SEQ ID NO 19
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 19

Ser Leu Leu Ile Ala Arg Arg Met Pro Asn Phe Asn
1               5                  10

<210> SEQ ID NO 20
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 20

Ser Lys Leu Val Gln Ala Ser Ala Ser Gly Val Asn
1               5                  10

<210> SEQ ID NO 21
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 21

Ser Ser Tyr Leu Lys Ala Ser Asp Ala Pro Asp Asn
1               5                  10

<210> SEQ ID NO 22
<211> LENGTH: 12
<212> TYPE: PRT
<213> ORGANISM: Artificial sequence
<220> FEATURE:
```

<223> OTHER INFORMATION: Synthetic polypeptide

<400> SEQUENCE: 22

Arg Pro Lys Pro Gln Gln Phe Phe Gly Leu Met Asn
1               5                   10

<210> SEQ ID NO 23
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 23

Ser Leu Arg Pro Leu Ala Leu Trp Arg Ser Phe Asn
1               5                   10

<210> SEQ ID NO 24
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 24

Ser Pro Gln Gly Ile Ala Gly Gln Arg Asn Phe Asn
1               5                   10

<210> SEQ ID NO 25
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 25

Asp Val Asp Glu Arg Asp Val Arg Gly Phe Ala Ser Phe Leu
1               5                   10

<210> SEQ ID NO 26
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 26

Ser Leu Pro Leu Gly Leu Trp Ala Pro Asn Phe Asn
1               5                   10

<210> SEQ ID NO 27
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 27

Ser Leu Leu Ile Phe Arg Ser Trp Ala Asn Phe Asn
1               5                   10

<210> SEQ ID NO 28
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 28

Ser Gly Val Val Ile Ala Thr Val Ile Val Ile Thr
1               5                   10

<210> SEQ ID NO 29
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 29

Ser Leu Gly Pro Gln Gly Ile Trp Gly Gln Phe Asn
1               5                   10

<210> SEQ ID NO 30
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 30

Lys Lys Ser Pro Gly Arg Val Val Gly Gly Ser Val
1               5                   10

<210> SEQ ID NO 31
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 31

Pro Gln Gly Leu Leu Gly Ala Pro Gly Ile Leu Gly
1               5                   10

<210> SEQ ID NO 32
<211> LENGTH: 31
<212> TYPE: PRT
<213> ORGANISM: Artificial sequence
<220> FEATURE:
<223> OTHER INFORMATION: Synthetic polypeptide

<400> SEQUENCE: 32

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 33
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 33

Gly Pro Gln Gly Leu Ala Gly Gln Arg Gly Ile Val
1               5                   10

<210> SEQ ID NO 34
<211> LENGTH: 12
<212> TYPE: PRT
<213> ORGANISM: Artificial sequence

```
<220> FEATURE:
<223> OTHER INFORMATION: Synthetic polypeptide

<400> SEQUENCE: 34

Gly Gly Ser Gly Gln Arg Gly Arg Lys Ala Leu Glu
1               5                   10

<210> SEQ ID NO 35
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 35

Ser Leu Ser Ala Leu Leu Ser Ser Asp Ile Phe Asn
1               5                   10

<210> SEQ ID NO 36
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 36

Ser Leu Pro Arg Phe Lys Ile Ile Gly Gly Phe Asn
1               5                   10

<210> SEQ ID NO 37
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 37

Ser Leu Leu Gly Ile Ala Val Pro Gly Asn Phe Asn
1               5                   10

<210> SEQ ID NO 38
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 38

Phe Phe Lys Asn Ile Val Thr Pro Arg Thr Pro Pro
1               5                   10

<210> SEQ ID NO 39
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 39

Cys Gln Pro Gln Gly Leu Ala Lys Cys
1               5

<210> SEQ ID NO 40
<211> LENGTH: 1000
<212> TYPE: DNA
<213> ORGANISM: Homo sapiens
```

<400> SEQUENCE: 40

```
agagcaaggg aaaggaactt cctccacctt cggggctgga gccctttttcc tctgcatctc       60
cagtctctga gtgaagatgg ggggcctgac agcctcggac gtacacccga ccctgggggt      120
ccagctcttc tcagctggaa tagcggcgtg cttggcggac gtgatcacct cccgctgga       180
cacggccaaa gtccggctcc aggtccaagg tgaatgcccg acgtccagtg ttattaggta      240
taaaggtgtc ctgggaacaa tcaccgctgt ggtaaaaaca gaagggcgga tgaaactcta      300
cagcgggctg cctgcggggc ttcagcggca aatcagctcc gcctctctca ggatcggcct      360
ctacgacacg gtccaggagt tcctcaccgc agggaaagaa acagcaccta gtttaggaag      420
caagatttta gctggtctaa cgactggagg agtggcagta ttcattgggc aacccacaga      480
ggtcgtgaaa gtcagacttc aagcacagag ccatctccac ggaatcaaac ctcgctacac      540
ggggacttat aatgcgtaca gaataatagc aacaaccgaa ggcttgacgg tctttggaa       600
agggactact cccaatctga tgagaagtgt catcatcaat tgtacagagc tagtaacata      660
tgatctaatg aaggaggcct ttgtgaaaaa caacatatta gcagatgacg tcccctgcca      720
cttggtgtcg gctcttatcg ctggattttg cgcaacagct atgtcctccc cggtggatgt      780
agtaaaaacc agatttatta attctccacc aggacagtac aaaagtgtgc ccaactgtgc      840
aatgaaagtg ttcactaacg aaggaccaac ggctttcttc aagggggttgg taccttcctt      900
cttgcgactt ggatcctgga acgtcattat gtttgtgtgc tttgaacaac tgaaacgaga      960
actgtcaaag tcaaggcaga ctatggactg tgccacataa                          1000
```

<210> SEQ ID NO 41
<211> LENGTH: 307
<212> TYPE: PRT
<213> ORGANISM: Homo sapiens

<400> SEQUENCE: 41

```
Met Gly Gly Leu Thr Ala Ser Asp Val His Pro Thr Leu Gly Val Gln
1               5                   10                  15

Leu Phe Ser Ala Gly Ile Ala Ala Cys Leu Ala Asp Val Ile Thr Phe
            20                  25                  30

Pro Leu Asp Thr Ala Lys Val Arg Leu Gln Val Gln Gly Glu Cys Pro
        35                  40                  45

Thr Ser Ser Val Ile Arg Tyr Lys Gly Val Leu Gly Thr Ile Thr Ala
    50                  55                  60

Val Val Lys Thr Glu Gly Arg Met Lys Leu Tyr Ser Gly Leu Pro Ala
65                  70                  75                  80

Gly Leu Gln Arg Gln Ile Ser Ser Ala Ser Leu Arg Ile Gly Leu Tyr
                85                  90                  95

Asp Thr Val Gln Glu Phe Leu Thr Ala Gly Lys Glu Thr Ala Pro Ser
            100                 105                 110

Leu Gly Ser Lys Ile Leu Ala Gly Leu Thr Thr Gly Gly Val Ala Val
        115                 120                 125

Phe Ile Gly Gln Pro Thr Glu Val Lys Val Arg Leu Gln Ala Gln
    130                 135                 140

Ser His Leu His Gly Ile Lys Pro Arg Tyr Thr Gly Tyr Asn Ala
145                 150                 155                 160

Tyr Arg Ile Ile Ala Thr Thr Glu Gly Leu Thr Gly Leu Trp Lys Gly
                165                 170                 175

Thr Thr Pro Asn Leu Met Arg Ser Val Ile Ile Asn Cys Thr Glu Leu
            180                 185                 190
```

```
Val Thr Tyr Asp Leu Met Lys Glu Ala Phe Val Lys Asn Asn Ile Leu
        195                 200                 205
Ala Asp Asp Val Pro Cys His Leu Val Ser Ala Leu Ile Ala Gly Phe
    210                 215                 220
Cys Ala Thr Ala Met Ser Ser Pro Val Asp Val Lys Thr Arg Phe
225                 230                 235                 240
Ile Asn Ser Pro Pro Gly Gln Tyr Lys Ser Val Pro Asn Cys Ala Met
                245                 250                 255
Lys Val Phe Thr Asn Glu Gly Pro Thr Ala Phe Phe Lys Gly Leu Val
                260                 265                 270
Pro Ser Phe Leu Arg Leu Gly Ser Trp Asn Val Ile Met Phe Val Cys
                275                 280                 285
Phe Glu Gln Leu Lys Arg Glu Leu Ser Lys Ser Arg Gln Thr Met Asp
                290                 295                 300
Cys Ala Thr
305
```

```
<210> SEQ ID NO 42
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 42

Cys Gly Gly Asn Gly Glu Pro Arg Gly Asp Thr Tyr Arg Ala Tyr
1               5                   10                  15

<210> SEQ ID NO 43
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 43

Cys Gly Gly Val Ser Trp Phe Ser Arg His Arg Tyr Ser Pro Phe Ala
1               5                   10                  15

Val Ser

<210> SEQ ID NO 44
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 44

Cys Gly Gly Asn Arg Trp His Ser Ile Tyr Ile Thr Arg Phe Gly
1               5                   10                  15

<210> SEQ ID NO 45
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 45

Cys Gly Gly Thr Trp Tyr Lys Ile Ala Phe Gln Arg Asn Arg Lys
1               5                   10                  15
```

COMPOSITIONS AND METHODS FOR PRODUCING AND ADMINISTERING BROWN ADIPOCYTES

CROSS-REFERENCE

This application is a national stage filing under 35 U.S.C. § 371 of PCT/US2014/069612, filed Dec. 10, 2014, which claims the benefit of U.S. Provisional Patent Application No. 61/914,672, filed Dec. 11, 2013, which applications are incorporated herein by reference in their entirety.

INCORPORATION BY REFERENCE OF SEQUENCE LISTING PROVIDED AS A TEXT FILE

A Sequence Listing is provided herewith as a text file, "BERK-230WO Seq List_ST25.txt" created on Nov. 30, 2014 and having a size of 15 KB. The contents of the text file are incorporated by reference herein in their entirety.

INTRODUCTION

The unabated growth of the obesity epidemic and associated diseases like type-2-diabetes reflects current lack of efficient strategies for intervention and treatment. Since obesity results from an imbalance in the ratio of energy intake to energy expenditure, it can be targeted either through reduced caloric uptake or by increasing energy consuming processes.

Adipose tissue plays a critical role in controlling whole-body energy balance. There are two types of adipose tissue: white adipose tissue (WAT), which is known as white fat and is composed of white adipocytes; and brown adipose tissue (BAT), which is known as brown fat and is composed of brown adipocytes. These two adipose tissues can be distinguished from each other based on their morphology, gene expression profile, and by characteristic biochemical functions. As the primary fuel reserve in mammals, WAT stores triacylglycerol (TAG) during times of energy surplus and hydrolyzes TAG (lipolysis) during times of energy deprivation to provide fatty acids (FAs) as fuel for other organs. BAT, on the other hand, is specialized in thermogenesis, using FAs generated through lipolysis as substrates for mitochondrial β-oxidation and to activate UCP-1. BAT possesses the inherent ability to dissipate metabolic energy as heat in a process termed non-shivering thermogenesis. The amount of BAT correlates inversely with body mass index (BMI), and variations in the amount of BAT can drive alterations in body weight.

Literature

Cannon et al., Physiol Rev. 2004 January; 84(1):277-359; Cypess et al., N Engl J Med. 2009 Apr. 9; 360(15):1509-17; van Marken Lichtenbelt et al., N Engl J Med. 2009 Apr. 9; 360(15):1500-8; Virtanen et al., N Engl J Med. 2009 Apr. 9; 360(15):1518-25; Ouellet et al., J Clin Endocrinol Metab. 2011 January; 96(1):192-9; Stanford et al., J Clin Invest. 2013 Jan. 2; 123(1):215-23; Himms-Hagen et al., Am J Physiol. 1994 April; 266(4 Pt 2):R1371-82; Ghorbani et al., Biochem Pharmacol. 1997 Jul. 1; 54(1):121-31; Tseng et al., Nature. 2008 Aug. 21; 454(7207):1000-4; Ohno et al., Cell Metab. 2012 Mar. 7; 15(3):395-404; Elabd et al., Stem Cells. 2009 November; 27(11):2753-60; Nishio et al., Cell Metab. 2012 Sep. 5; 16(3):394-406; Rodeheffer et al., Cell. 2008 Oct. 17; 135(2):240-9; Ahfeldt et al., Nat Cell Biol. 2012 Jan. 15; 14(2):209-19; Schulz et al., Proc Natl Acad Sci USA. 2011 Jan. 4; 108(1):143-8.

SUMMARY

The present disclosure provides compositions comprising a hydrogel and a cell adhesion ligand that together enhance the differentiation of cells (e.g., adipose derived mesenchymal stem cells (ADMSCs)) into brown adipocytes, and/or enhances the maintenance of brown adipocytes, and/or enhances the viability and metabolic activity of brown adipocytes. The present disclosure also provides methods of making and using the subject compositions.

In one aspect, provided herein is a composition comprising a hydrogel and a cell adhesion ligand that is covalently or non-covalently associated with the hydrogel. In certain embodiments, the cell adhesion ligand described herein is a syndecan-1 ligand. In some cases, the cell adhesion ligand includes the amino acid sequence RKRLQVQLSIRT (SEQ ID NO:1). In certain embodiments, the cell adhesion ligand described herein is an $\alpha_5\beta_{1/3}$ integrin ligand. In some cases, the cell adhesion ligand includes the amino acid sequence KAFDITYVRLKF (SEQ ID NO:2). In some cases, the composition comprises two or more different cell adhesion ligands. In some cases, the composition comprises a syndecan-1 ligand and an $\alpha_5\beta_{1/3}$ integrin ligand. In some such cases, the molar ratio of the syndecan-1 ligand to the $\alpha_5\beta_{1/3}$ integrin ligand present in the composition is in a range of from 1:1 to 1:5. In some such cases, the molar ratio of the syndecan-1 ligand to the $\alpha_5\beta_{1/3}$ integrin ligand present in the composition is 1:3.

In certain embodiments, the hydrogel polymer is a hyaluronic acid (HyA) polymer. In specific embodiments, the hydrogel polymer is an acrylated hyaluronic acid (HyA) polymer. In some embodiments, the hydrogel includes a proteolytically cleavable cross-linker that links one or more hydrogel polymers of the plurality of hydrogel polymers to another hydrogel polymer of the plurality. In specific embodiments, the cleavable cross-linker is a thiolated cross linker peptide. In some cases, the cleavable cross-linker is cleaved by a matrix metalloproteinase (MMP). In some cases, the hydrogel has a modulus in a range of from 5 pascals (Pa) to 500 kilopascals (kPa). In some cases, the hydrogel is thermopolymerizable.

In some embodiments, the hydrogel includes a factor release molecule conjugated to one or more hydrogel polymers. In certain embodiments, the cell adhesion ligand and the factor release molecule are conjugated to the same hydrogel polymer. In other embodiments, the cell adhesion ligand and the factor release molecule are conjugated to different hydrogel polymers. In certain embodiments of the hydrogel cell matrix, the factor release molecule is heparin.

In some embodiments, the composition comprises an enhancement compound that enhances the differentiation of cells (e.g., ADMSCs) to into brown adipocytes or enhances the maintenance of brown adipocytes. In some embodiments, the enhancement compound is selected from the group consisting of: VEGF, BMP7, SHH, BNP, BDNF, FGF21, TGFβ, Wnt10b, 1-methyl-3-isobutylxanthine (IBMX), insulin, 3,3',5 Triiodothyronine (T3), dexamethasone, rosiglitazone, and a combination thereof. In some embodiments, the enhancement compound is covalently or non-covalently bound to one or more hydrogel polymers. In certain embodiments, one or more enhancement compounds is non-covalently bound to a factor release molecule. In some cases, a factor release molecule allows for the controlled release or presentation of one or more enhancement compounds.

In another aspect, the composition comprises cells (e.g., WAT-MSCs, ADMSCs, brown adipocytes, etc.) embedded within the hydrogel (i.e., encapsulated in the polymer network). In some embodiments, the concentration of cells (e.g., cells per ml of hydrogel) embedded within the hydrogel is $1 \times 10^5$ cells/ml or more. In some cases, the cells are ADMSCs. In some cases, the ADMSCs are white adipose tissue derived mesenchymal stem cells (WAT-MSCs).

In another aspect, provided herein is a method of increasing the number of brown adipocytes in an individual, where the method includes implanting into the individual a composition that includes a hydrogel and a cell adhesion ligand that enhances the differentiation of cells (e.g., adipose derived mesenchymal stem cells (ADMSCs)) into brown adipocytes, and/or enhances the maintenance of brown adipocytes. In some embodiments, the composition includes an enhancement compound that enhances the differentiation of cells (e.g., ADMSCs) into brown adipocytes or enhances the maintenance of brown adipocytes. In some cases, the composition provides for the in vivo differentiation of endogenous stem cells into brown adipocytes. In some embodiments, the implanted composition includes brown adipocytes. In some embodiments, the implanted composition includes ADMSCs and at least 10% of the ADMSCs differentiate into brown adipocytes, thereby increasing the number of brown adipocytes in the individual.

In some embodiments, a method of increasing the number of brown adipocytes in an individual includes (a) culturing ADMSCs in the absence of hydrogel in a first differentiation medium for a period of time in a range of from 6 hours to 7 days, in the presence of a cell adhesion ligand, where the first differentiation medium comprises at least one enhancement compound that enhances the differentiation of ADMSCs to into brown adipocytes or enhances the maintenance of brown adipocytes, thereby producing a population of primed ADMSCs; (b) culturing the population of primed ADMSCs (under conditions and for a time period that provide for differentiation of at least 30% of the cells into brown adipocytes) with a composition that includes a hydrogel and a cell adhesion ligand that enhances the differentiation of adipose derived mesenchymal stem cells (ADMSCs) into brown adipocytes, and/or enhances the maintenance of brown adipocytes, thereby producing a cell-loaded hydrogel composition; and (c) implanting the cell-loaded hydrogel composition into the individual.

In some embodiments, a method of increasing the number of brown adipocytes in an individual includes (a) culturing ADMSCs in the absence of hydrogel in a first differentiation medium for a period of time in a range of from 6 hours to 7 days, in the absence of a cell adhesion ligand, where the first differentiation medium comprises at least one enhancement compound that enhances the differentiation of ADMSCs to into brown adipocytes or enhances the maintenance of brown adipocytes, thereby producing a population of primed ADMSCs; (b) culturing the population of primed ADMSCs (under conditions and for a time period that provide for differentiation of at least 30% of the cells into brown adipocytes) with a composition that includes a hydrogel and a cell adhesion ligand that enhances the differentiation of adipose derived mesenchymal stem cells (ADMSCs) into brown adipocytes, and/or enhances the maintenance of brown adipocytes, thereby producing a cell-loaded hydrogel composition; and (c) implanting the cell-loaded hydrogel composition into the individual.

In some embodiments, for methods of increasing the number of brown adipocytes in an individual, the hydrogel includes a factor release molecule conjugated to one or more hydrogel polymers. In some cases, the ADMSCs are autologous ADMSCs obtained from the individual. In some cases, the methods further include obtaining the autologous ADMSCs from the individual (e.g., via liposuction). In some cases, implanting includes injecting the composition into the individual (e.g., prior to gelation of the hydrogel).

Methods of increasing the number of brown adipocytes in an individual can provide for reduction of blood glucose to within a normal range, increased insulin sensitivity, increased metabolic rate, weight loss, and/or supplementation of endogenous heat production. Methods of increasing the number of brown adipocytes in an individual can elicit an anti-hyperglycemic effect. In some cases, administering a subject composition is performed in combination with administering to the individual at least one additional treatment regimen (e.g., a reduced calorie diet, administration of an agent that lowers blood glucose or increases insulin sensitivity, and the like) for treatment of a disorder.

In another aspect, provided herein is a method of inducing ADMSCs to differentiate into brown adipocytes, where the method includes culturing ADMSCs (under conditions and for a time period that provide for differentiation of at least 30% of the ADMSCs into brown adipocytes) with a composition that includes a hydrogel and a cell adhesion ligand that enhances the differentiation of adipose derived mesenchymal stem cells (ADMSCs) into brown adipocytes, and/or enhances the maintenance of brown adipocytes. In some cases, the method comprises, prior to culturing ADMSCs with a composition that includes a hydrogel, culturing ADMSCs in the absence of hydrogel in a first differentiation medium for a period of time in a range of from 6 hours to 7 days, in the presence of a cell adhesion ligand, where the first differentiation medium comprises at least one enhancement compound that enhances the differentiation of ADMSCs to into brown adipocytes or enhances the maintenance of brown adipocytes.

In some embodiments, the composition includes an enhancement compound that enhances the differentiation of ADMSCs to into brown adipocytes or enhances the maintenance of brown adipocytes. In some embodiments, the hydrogel includes a factor release molecule conjugated to one or more hydrogel polymers. In some cases, the culturing occurs in vitro. In some cases, the culturing occurs in vivo. In some cases, the method further comprises introducing the composition comprising brown adipocytes into an individual.

DEFINITIONS

Figure 1A:
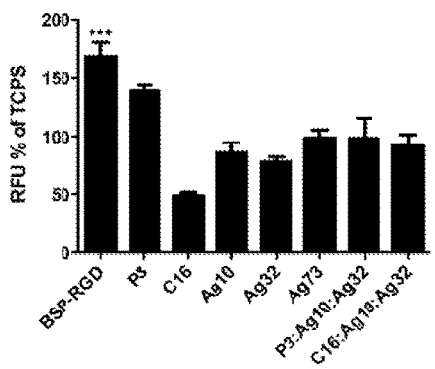
FIGS. 1A-F depict the effects of cell adhesion ligands on ADMSC differentiation into brown adipocytes.
Figure 1B:
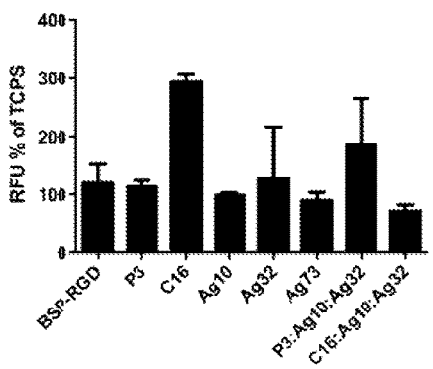

As used herein, the term "adipose tissue" refers to fat including the connective tissue that stores fat. Adipose tissue contains multiple regenerative cell types, including ADM- SCs and endothelial progenitor and precursor cells. Adipose tissue is located beneath the skin (subcutaneous fat), around internal organs (visceral fat), in bone marrow (yellow bone marrow) and in breast tissue. Specific locations of the body where adipose tissue is found are referred to as adipose depots.

The terms "subject," "individual," "host," and "patient" are used interchangeably herein to a member or members of any mammalian or non-mammalian species. Individuals, subjects and patients thus include, without limitation, humans, non-human primates, canines, felines, ungulates (e.g., equine, bovine, swine (e.g., pig)), rodents (e.g., rats, mice), and other subjects. Non-human animal models, particularly mammals, e.g. a non-human primate, a murine (e.g., a mouse, a rat), lagomorpha, etc. may be used for experimental investigations.

"Treating" or "treatment" of a condition or disease includes: (1) preventing at least one symptom of the condition, i.e., causing a clinical symptom to not significantly develop in a mammal that may be exposed to or predisposed to the disease but does not yet experience or display symptoms of the disease, (2) inhibiting the disease, i.e., arresting or reducing the development of the disease and/or its symptoms, or (3) relieving the disease, i.e., causing regression of the disease and/or its clinical symptoms.

A "therapeutically effective amount" or "efficacious amount" means the amount of a compound that, when administered to a mammal or other subject for treating a disease, is sufficient, in combination with another agent, or alone in one or more doses, to effect such treatment for the disease. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present disclosure depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, the term "label moiety" is intended to mean one or more atoms that can be specifically detected to indicate the presence of a substance to which the one or more atom is attached. A label moiety can be a primary label that is directly detectable or secondary label that can be indirectly detected, for example, via interaction with a primary label. Exemplary primary labels include, without limitation, an isotopic label such as a naturally non-abundant heavy isotope or radioactive isotope, examples of which include $^{14}C$, $^{123}I$, $^{124}I$, $^{125}I$, $^{131}I$, $^{32}P$, $^{35}S$ or $^{3}H$; optically detectable moieties such as a chromophore, luminophore, fluorophore, quantum dot or nanoparticle; electromagnetic spin label; calorimetric agent; magnetic substance; electron-rich material such as a metal; electrochemiluminescent label such as $Ru(bpy)_3^{2+}$; moiety that can be detected based on a nuclear magnetic, paramagnetic, electrical, charge to mass, or thermal characteristic; or light scattering or plasmon resonant materials such as gold or silver particles. Fluorophores that are useful in the invention include, for example, fluorescent lanthanide complexes, including those of Europium and Terbium, fluorescein, fluorescein isothiocyanate, carboxyfluorescein (FAM), dichlorotriazinylamine fluorescein, rhodamine, tetramethylrhodamine, umbelliferone, eosin, erythrosin, coumarin, methyl-coumarins, pyrene, Malacite green, Cy3, Cy5, stilbene, Lucifer Yellow, Cascade Blue™, Texas Red, alexa dyes, dansyl chloride, phycoerythin, green fluorescent protein and its wavelength shifted variants (e.g., yellow, red, blue, cyan, far red, cherry, tomato, tangerine, and the like), bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an adipose derived mesenchymal stem cell (ADMSC)" includes a plurality of such ADMSCs and reference to "the cell adhesion ligand" includes reference to one or more cell adhesion ligands and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Provided herein are compositions having a hydrogel and a cell adhesion molecule that enhances at least one of: the differentiation of adipose derived mesenchymal stem cells (ADMSCs) into brown adipocytes; and the maintenance of brown adipocytes. Also provided are methods of making and using the subject compositions.

Compositions

Aspects of the disclosure include compositions comprising a hydrogel and a cell adhesion ligand.

Hydrogels

A hydrogel includes a plurality of hydrogel polymers. Any suitable hydrogel polymers can be used in the hydrogel compositions provided herein. Hydrogel polymers may include one or more of a monomer, including, but not limited to: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers.

Because the addition of a crosslinking agent (i.e., a cross-linker) can cause gelation of the hydrogel composition (i.e., can result in a phase change of the composition from liquid to gel), in cases where a subject composition includes cells, a cross-linker can be added to the composition before or after the cells are added to the hydrogel. In cases where a subject composition is implanted into an individual, a cross-linker can be added before implantation (e.g., causing gelation before implantation, for surgical implantation, or facilitating gelation shortly after the addition of the cross-linker, e.g., for injection protocols where the composition is injected in liquid form but becomes a gel shortly after injection). Alternatively, a cross-linker may be added simultaneous with (e.g., double barrel injector), or after implantation (e.g., after initial injection of the composition).

The hydrogel polymer that encapsulates a cell (e.g., an ADMSC, a brown adipocyte, etc.) is generally hydrophilic. Suitable hydrogel polymers include, but are not limited to, poly(N-isopropylacrylamide) (pNIPAAm); poly(N-isopropylacrylamide-co-acrylic acid); hyaluronic acid or hyaluronate; crosslinked hyaluronic acid or hyaluronate; pHEMA; or copolymers of p(NIPAAm)-based sIPNs and other hydrogel sIPNs (semi-interpenetrating networks). In certain embodiments, the hydrogel polymer is a hyaluronic acid (HyA) polymer, which is a natural glycosaminoglycan (GAG) biopolymer with a variety of favorable biological properties. In some embodiments, the hydrogel polymer is an acrylated hyaluronic acid (HyA) polymer.

The storage modulus (i.e., material stiffness, also referred to herein as "modulus") of a hydrogel can be in the range of from 5 pascals (Pa) to 500 kilopascals (kPa) (e.g., from 100 Pa to 400 kPa, from 300 Pa to 400 kPa, from 300 Pa to 50 kPa, from 300 Pa to 30 kPa, from 300 Pa to 20 kPa, from 300 Pa to 15 kPa, from 400 Pa to 300 kPa, from 500 Pa to 200 kPa, from 500 Pa to 100 kPa, from 500 Pa to 50 kPa, from 500 Pa to 25 kPa, from 500 Pa to 20 kPa, from 500 Pa to 15 kPa, from 500 Pa to 10 kPa, from 750 Pa to 10 kPa, from 800 Pa to 10 kPa, from 900 Pa to 10 kPa, from 1 kPa to 10 kPa, from 2 kPa to 10 kPa, from 3 kPa to 10 kPa, from 2 kPa to 9 kPa, from 3 kPa to 9 kPa, from 500 Pa to 5 kPa, from 500 Pa to 3 kPa, or from 500 Pa to 2 kPa).

In some cases, a subject hydrogel is thermopolymerizable. Thus, in some cases, gelation (i.e., polymerization) of a subject hydrogel can be temperature sensitive. In some cases, a subject hydrogel is liquid at room temperature and polymerizes at an increased temperature (e.g., body temperature). For example, in some cases a subject hydrogel composition can be implanted (e.g., injected) into an individual in liquid form, and because the hydrogel is thermopolymerizable, the hydrogel polymerizes (i.e., transitions into a gel-like state) once inside the individual (e.g., once exposed to body temperature) (e.g., immediately, within minutes, within hours, within days, etc.).

In some embodiments, the hydrogel is a temperature-sensitive hydrogel. In some embodiments, a temperature-sensitive hydrogel is a polyacrylic acid or derivative thereof, e.g., poly (N-isopropylacrylamide). Alternatively, the temperature-sensitive hydrogel is an interpenetrating hydrogel network of poly(acrylamide) and poly(acrylic acid), and the increase in temperature causes the hydrogel to swell.

In some embodiments (described in more detail below), a subject composition comprises a hydrogel, a cell adhesion ligand (e.g., conjugated to one or more hydrogel polymers), and one or more of: a factor release molecule (e.g., conjugated to one or more hydrogel polymers); an enhancement compound; and a cross-linker (e.g., a proteolytically cleavable cross-linker peptide) that links one or more hydrogel polymers of the plurality of hydrogel polymers to another hydrogel polymer of the plurality.

Suitable hydrogels and hydrogel compositions are also described in U.S. applications 20040001892, 20130184235, 20130183349, 20130276669, 20130267455, 20130244943, 20130136697, 20130129835, 20130129800, 20130045242, 20130012913, and 20130004546; all of which are hereby incorporated by reference in their entirety.

Cell Adhesion Ligand

A subject composition comprising a cell adhesion ligand conjugated to a hydrogel polymer. Suitable cell adhesion ligands provide for binding to a cell surface receptor on the surface of a cell, e.g., a WAT-MSC, a brown adipocyte, an adipose derived mesenchymal stem cell (ADMSC). In certain embodiments, the cell adhesion ligand is a cell adhesion peptide. Any suitable cell adhesion peptide can be used. A suitable cell adhesion ligand enhances at least one of: (i) the differentiation of adipose derived mesenchymal stem cells (ADMSCs) into brown adipocytes; and (ii) the maintenance of brown adipocytes. In certain embodiments, the cell adhesion peptide can bind an integrin. In specific embodiments, the cell adhesion peptide can bind $\alpha_5\beta_1$ integrin and $\alpha_5\beta_3$ integrin (referred to as $\alpha_5\beta_{1/3}$ integrin).

In certain embodiments, the cell adhesion peptide is 40 amino acids or less, 35 amino acids or less, 30 amino acids or less, 25 amino acids or less, or 20, 19, 18, 17, 16, 15, 14, 13, 12, 11, 10, 9, 8, 7, 6, or 5 amino acids or less. In some cases, the cell adhesion peptide has a length of from about 5 amino acids (aa) to about 40 aa, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, or from about 35 aa to about 40 aa.

In some embodiments, the cell adhesion ligand is an adhesion ligand for syndecan-1. An example of a suitable adhesion ligand for syndecan-1 includes the amino acid sequence: RKRLQVQLSIRT (SEQ ID NO:1). In some embodiments, the cell adhesion ligand is an adhesion ligand for $\alpha_5\beta_{1/3}$ integrin. An example of a suitable adhesion ligand for $\alpha_5\beta_{1/3}$ integrin includes the amino acid sequence: KAFDITYVRLKF (SEQ ID NO:2). Other suitable peptides are shown in Table 1, below.

TABLE 1

Exemplary suitable cell adhesion ligands. Peptide targets for integrins and other adhesion receptors present on stem and progenitor cells identified via RT- PCR, immunofluorescence, confocal microscopy, or flow cytometry.

| Peptide | Peptide name | An adhesion ligand for: | SEQ ID NO: |
|---|---|---|---|
| RKRLQVQLSIRT | AG73 | syndecan-1 | 1 |
| KAFDITYVRLKF | C16 | $\alpha_5\beta_{1/3}$ integrin ($\alpha_5\beta_1$ and $\alpha_5\beta_3$) | 2 |
| TWYKIAFQRNRK | AG32 | $\alpha_6\beta_1$ integrin | 3 |
| NGEPRGDTYRAY | bsp-RGD(15) | $\alpha_5\beta_3$ integrin | 4 |
| NRWHSIYITRFG | AG10 | $\alpha_6\beta_1$ integrin | 5 |
| EILDVPST | LDVP | $\alpha_4\beta_1$ integrin | 6 |
| VSWFSRHRYSPFAVS | P3 | $\alpha_6\beta_1$ integrin | 7 |

In some cases, the cell adhesion ligand has an amino acid sequence of CGG on the N terminal side of the peptide sequence (e.g., to allow for conjugation of the peptide to a hydrogel polymer). For example, any of the sequences set forth in SEQ ID NOs: 1-7 can have a CGG sequence to the N terminal side of the sequence. As an illustrative example, CGGRKRLQVQLSIRT (SEQ ID NO: 8) is a cell adhesion ligand having a CGG to the N terminal side of the peptide sequence set forth as SEQ ID NO: 1 and CGGKAFDITYVRLKF (SEQ ID NO: 9) is a cell adhesion ligand having a CGG to the N terminal side of the peptide sequence set forth as SEQ ID NO: 2. Suitable exemplary CGG-containing cell adhesion ligands are set forth in SEQ ID NOs: 8-14, which correspond to the non CGG-containing cell adhesion ligands set forth in SEQ ID NOs: 1-7. In some cases, the peptide comprises an RGD sequence, e.g., the cell adhesion peptide comprises an RGD sequence. In some cases, an RGD sequence is specifically excluded.

In some embodiments, a subject composition has two or more cell adhesion ligands. The ratio of the two or more cell adhesion ligands does not have to be 1:1 and the ligands can be present in any convenient ratio. For example, in some cases where a subject composition includes two adhesion ligands, the first and second cell adhesion ligands are present in the composition in a ratio in a range of from 10:1 to 1:10 (e.g., 10:1 to 8:1, 9:1 to 7:1, 8:1 to 6:1, 7:1 to 3:1, 6:1 to 4:1, 6:1 to 3:1, 5:1 to 2:1, 5:1 to 3:1, 4:1 to 2:1, 4:1 to 1:1, 3:1 to 1:1, 1:1 to 1:5, 1:1 to 1:3, 1:2 to 1:4, 1:2.5 to 1:3.5, 1:2 to 1:5, 1:3 to 1:5, 1:3 to 1:6, 1:4 to 1:6, 1:5 to 1:7, 1:6 to 1:8, 1:7 to 1:10, or 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10).

For example, in some cases, a subject composition has a ligand for syndecan-1 and a ligand for $\alpha_5\beta_{1/3}$ integrin. In some cases, a subject composition has a ligand for syndecan-1 that includes the amino acid sequence: RKRLQVQLSIRT (SEQ ID NO:1) and a ligand for $\alpha_5\beta_{1/3}$ integrin that includes the amino acid sequence: KAFDITYVRLKF (SEQ ID NO:2). In some cases, a subject composition has a ligand for syndecan-1 that includes the amino acid sequence: CGGRKRLQVQLSIRT (SEQ ID NO:8) and a ligand for $\alpha_5\beta_{1/3}$ integrin that includes the amino acid sequence: CGGKAFDITYVRLKF (SEQ ID NO:9). In some cases, the ratio of the syndecan-1 ligand to the $\alpha_5\beta_{1/3}$ integrin ligand is present in the composition in a range of from 10:1 to 1:10 (e.g., 10:1 to 8:1, 9:1 to 7:1, 8:1 to 6:1, 7:1 to 3:1, 6:1 to 4:1, 6:1 to 3:1, 5:1 to 2:1, 5:1 to 3:1, 4:1 to 2:1, 4:1 to 1:1, 3:1 to 1:1, 1:1 to 1:3, 1:2 to 1:4, 1:2.5 to 1:3.5, 1:2 to 1:5, 1:3 to 1:5, 1:3 to 1:6, 1:4 to 1:6, 1:5 to 1:7, 1:6 to 1:8, 1:7 to 1:10, or 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10). In some cases, the ratio of the syndecan-1 ligand to the $\alpha_5\beta_{1/3}$ integrin ligand is present in the composition in a range of from 1:2 to 1:4 (e.g., 1:2.5 to 1:3.5, or 1:3).

A cell adhesion ligand can be present in a subject composition at a concentration (e.g., total combined concentration when two or more cell adhesion ligands are present) in a range of from 0.1 µg/ml to 100 µg/ml (e.g., 0.5 µg/ml to 75 µg/ml, 0.75 µg/ml to 50 µg/ml, 1 µg/ml to 25 µg/ml, 1 µg/ml to 20 µg/ml, 2.5 µg/ml to 17.5 µg/ml, 5 µg/ml to 12 µg/ml, 7.5 µg/ml to 12 µg/ml, 8 µg/ml to 11 µg/ml, 8 µg/ml to 10 µg/ml).

Enhancement Compound

In some embodiments, the composition includes an enhancement compound that enhances the differentiation of ADMSCs into brown adipocytes or enhances the maintenance of brown adipocytes. In some cases, the enhancement compound is selected from: vascular endothelial growth factor (VEGF), bone morphogenic protein-7 (BMP7), sonic hedgehog polypeptide (SHH), brain natriuretic peptide (BNP), brain-derived neurotrophic factor (BDNF), fibroblast growth factor 21 (FGF21), transforming growth factor-β (TGFβ), Wnt10b, insulin, 1-methyl-3-isobutylxanthine (isobutylmethylxanthine) (IBMX), 3,3',5 triiodothyronine (T3), dexamethasone (Dex), rosiglitazone, and a combination thereof. In some cases, the enhancement compound includes insulin, T3, Dex, and IBMX. In some cases, the enhancement compound includes insulin and rosiglitazone. In some cases, the enhancement compound includes insulin, T3, Dex, IBMX, and a growth factor. In some cases, the enhancement compound includes insulin, rosiglitazone, and a growth factor. In some cases, the growth factor is selected from VEGF, BMP7, SHH, BNP, BDNF, FGF21, TGFβ, Wnt10b, and insulin (see Table 2).

TABLE 2

Exemplary suitable growth factors

| Factor name | Alternative names | Sequence identifiers (cDNA and protein) (including isoforms) |
|---|---|---|
| VEGF | vascular endothelial growth factor A, VEGFA | NM_001025366.2; NM_001025367.2; NM_001025368.2; NM_001025369.2; NM_001025370.2; NM_001033756.2; NM_001171622.1; NM_001171623.1; NM_001171624.1; NM_001171625.1; NM_001171626.1; NM_001171627.1; NM_001171628.1; NM_001171629.1; NM_001171630.1; NM_001204384.1; NM_001204385.1; NM_003376.5; NP_001020537.2; NP_001020538.2; NP_001020539.2; NP_001020540.2; NP_001020541.2; NP_001028928.1; NP_001165093.1; NP_001165094.1; NP_001165095.1; NP_001165096.1; NP_001165097.1; NP_001165098.1; NP_001165099.1; NP_001165100.1; NP_001165101.1; NP_001191313.1; NP_001191314.1; NP_003367.4 |
| BMP7 | bone morphogenetic protein 7 | NM_001719.2; NP_001710.1 |
| SHH | sonic hedgehog | NM_000193.2; NP_000184.1 |
| BNP | NPPB; natriuretic peptide B | NM_002521.2; NP_002512.1 |
| BDNF | brain-derived neurotrophic factor | NM_001143805.1; NM_001143806.1; NM_001143807.1; NM_001143808.1; NM_001143809.1; NM_001143810.1; NM_001143811.1; NM_001143812.1; NM_001143813.1; NM_001143814.1; NM_001143816.1; NM_001709.4; NM_170731.4; NM_170732.4; NM_170733.3; NM_170734.3; NM_170735.5; NP_001137277.1; NP_001137278.1; NP_001137279.1; NP_001137280.1; NP_001137281.1; NP_001137282.1; NP_001137283.1; NP_001137284.1; NP_001137285.1; NP_001137286.1; NP_001137288.1; NP_001700.2; NP_733927.1; NP_733928.1; NP_733929.1; NP_733930.1; NP_733931.1 |
| FGF21 | fibroblast growth factor 21 | NM_019113.2; NP_061986.1 |
| TGFβ | transforming growth factor, beta 1, TGFB1 | NM_000660.5; NP_000651.3 |
| Wnt10b | wingless-type MMTV integration site family, member 10B | NM_003394.3; NP_003385.2 |
| Insulin | INS, IDDM2, ILPR, IRDN, MODY10 | NM_000207.2; NM_001185097.1; NM_001185098.1; NP_000198.1; NP_001172026.1; NP_001172027.1 |

In some embodiments, the enhancement compound is present in the composition at a concentration in a range of from 5 ng/ml to 150 ng/ml (e.g., 5 ng/ml to 125 ng/ml, 5 ng/ml to 100 ng/ml, 5 ng/ml to 80 ng/ml, 5 ng/ml to 60 ng/ml, 5 ng/ml to 50 ng/ml, 5 ng/ml to 40 ng/ml, 5 ng/ml to 35 ng/ml, 10 ng/ml to 30 ng/ml, 15 ng/ml to 25 ng/ml, 17.5 ng/ml to 22.5 ng/ml, or 20 ng/ml). In some cases, the enhancement factor is BMP7.

As stated above, in some cases, the enhancement compound is a growth factor. As used herein, the term "growth factor" is used broadly to encompass factors that modulate the growth, proliferation, survival, differentiation, and/or function of a cell. Suitable growth factors include, but are not limited to: a colony stimulating factor (e.g., Neupogen® (filgrastim, G-CSF), Neulasta (pegfilgrastim), granulocyte colony stimulating factor (G-CSF), granulocyte-monocyte colony stimulating factor, macrophage colony stimulating factor, megakaryocyte colony stimulating factor, and the like), a growth hormone (e.g., a somatotropin, e.g., Genotropin®, Nutropin®, Norditropin®, Saizen®, Serostim®, Humatrope®, a human growth hormone, and the like), an interleukin (e.g., IL-1, IL-2, including, e.g., Proleukin®, IL-3, IL-4, IL-5, IL-6, IL-7, IL-8, IL-9, etc.), a growth factor (e.g., Regranex® (beclapermin, PDGF), Fiblast® (trafermin, bFGF), Stemgen® (ancestim, stem cell factor), keratinocyte growth factor, an acidic fibroblast growth factor, a stem cell factor, a basic fibroblast growth factor, a hepatocyte growth factor (HGF), and the like), a chemokine (e.g., IP-10, Mig, Groα/IL-8, RANTES, MIP-1α, MIP-1β, MCP-1, PF-4, and the like), an angiogenic agent (e.g., vascular endothelial growth factor (VEGF)), an EGF (epidermal growth factor), a receptor tyrosine kinase ligand, thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, a tissue factor, an insulin-like growth factor, a luteinizing hormone, a follicle stimulating hormone, a macrophage activating factor, tumor necrosis factor, a neutrophil chemotactic factor, a nerve growth factor, a tissue inhibitor of metalloproteinases, a vasoactive intestinal peptide, angiogenin, angiotropin, fibrin, hirudin, a leukemia inhibitory factor, a Wnt signaling ligand (e.g., Wnt, norrin, R-spondin, etc.), a Wnt signaling inhibitor (e.g, WIF (Wnt inhibitory factor), sFRP (Secreted Frizzled Related Protein), Dkk (Dickkopf), Notum, and the like), a Notch or Notch ligand protein, a receptor tyrosine kinase ligand, a hedgehog (HH) pathway ligand (e.g., HH), and a transforming growth factor-β (TGF-β) In certain embodiments, the factor is a cell growth factor. In some cases, the growth factor is selected from VEGF, BMP7, SHH, BNP, BDNF, FGF21, TGFβ, Wnt10b and a combination of two or more thereof.

Factor Release Molecule

A hydrogel polymer present in a subject composition can be conjugated to a factor release molecule that allows for the controlled release and delivery of a factor non-covalently bound to the factor release molecule at a predictable rate. In some cases, a fraction (e.g., 10%, 20%, 30%, 40%, 50%, 60%, 70%, 80%, 90%, or 100%) of factors (e.g., a population of factors, where all members of the population are the same type of factor or where the population comprises two or more different factors) that are non-covalently bound to the factor release molecules are "released" (i.e., are no longer bound to the factor release molecule) over time (e.g., over a period of 7 days, 10 days, 12 days, 15 days, 20 days, 25 days, or 30 days). In some cases, the rate of factor release is predictable (e.g., the rate has already been calculated for a particular factor in combination with a particular hydrogel matrix or particular release factor). In some cases, the rate of factor release can be controlled (e.g., experimentally manipulated) using methods known by one of ordinary skill in the art (e.g., using a cleavable linker to bind the factor to the factor release molecule, using a molecule to out-compete the factor for binding to the factor release molecule, etc.). Cells being cultured on the hydrogel matrix are then exposed to (i.e., are contacted with, are free to bind to) the released factors.

In some cases, cells being cultured with a subject hydrogel composition can bind to factors that are still non-covalently bound to the factor release molecules. Thus, the factor release molecule, and therefore the hydrogel matrix, can be said to "present" a factor (e.g., a factor that is non-covalently bound to the factor release molecule) to a cell.

Any suitable factor release molecules may be used. In some embodiments, the factor release molecule is a polysaccharide. In specific embodiments, the factor release molecule is glycosaminoglycan. In some embodiments, the factor release molecule is heparin, which can bind to a large number of cell secreted factors (e.g., growth factors).

In certain embodiments, a subject composition includes one or more factors that can be bound to, released and delivered ("presented") to a cell encapsulated by the hydrogel in a controlled manner. Factors that are bound and released by the factor release molecule can be any factor that modulates (e.g., increases or decreases) the growth, proliferation, survival, differentiation (e.g., a factor that promotes differentiation; a factor that inhibits differentiation; and the like), and/or function of a cell encapsulated by the hydrogel. For example a suitable factor that can bind to a factor release molecule is an enhancement compound (described above).

In certain embodiments, a cell adhesion ligand and a factor release molecule are conjugated to the same hydrogel polymer in the hydrogel. In other embodiments, a cell adhesion ligand and a factor release molecule are conjugated to different hydrogel polymers in the hydrogel.

Cross-linkers

In certain embodiments, the hydrogel polymers of the hydrogel are linked to each other by a cross-linker (e.g., a cross-linker peptide). In certain embodiments, the hydrogel polymer is linked to one another with a proteolytically cleavable cross-linker polypeptide. See, e.g., Kim and Healy (2003) *Biomacromolecules* 4:1214. Such proteolytically cleavable cross-linker polypeptides allow for the remodeling of the hydrogel cell matrix. Examples of proteolytically cleavable cross-linker polypeptides can be or include, but are not limited to, a matrix metalloproteinase (MMP) cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue), e.g., Pro-X-X-Hy-(Ser/Thr), e.g., Pro-Leu/Gln-Gly-Met-Thr-Ser (SEQ ID NO:15) or Pro-Leu/Gln-Gly-Met-Thr (SEQ ID NO:16). Another example of a protease cleavage site is a plasminogen activator cleavage site, e.g., a urokinase plasminogen activator (uPA) or a tissue plasminogen activator (tPA) cleavage site. Specific examples of cleavage sequences of uPA and tPA include sequences comprising Val-Gly-Arg. Another example is a thrombin cleavage site, e.g., CGLVPAGSGP (SEQ ID NO:17). Additional suitable linkers comprising protease cleavage sites include linkers comprising one or more of the following amino acid sequences: 1) SLLKSRMVPNFN (SEQ ID NO:18) or SLLIARRMPNFN (SEQ ID NO:19), cleaved by cathepsin B; SKLVQASASGVN (SEQ ID NO:20) or SSYLKAS-DAPDN (SEQ ID NO:21), cleaved by an Epstein-Barr virus protease; RPKPQQFFGLMN (SEQ ID NO:22) cleaved by MMP-3 (stromelysin); SLRPLALWRSFN (SEQ ID NO:23) cleaved by MMP-7 (matrilysin); SPQGIAGQRNFN (SEQ ID NO:24) cleaved by MMP-9; DVDERDVRGFASFL SEQ ID NO:25) cleaved by a thermolysin-like MMP; SLPLGL-WAPNFN (SEQ ID NO:26) cleaved by matrix metalloproteinase 2 (MMP-2); SLLIFRSWANFN (SEQ ID NO:27) cleaved by cathespin L; SGVVIATVIVIT (SEQ ID NO:28) cleaved by cathespin D; SLGPQGIWGQFN (SEQ ID NO:29) cleaved by matrix metalloproteinase 1 (MMP-1); KKSPGRVVGGSV (SEQ ID NO:30) cleaved by urokinase-type plasminogen activator; PQGLLGAPGILG (SEQ ID NO:31) cleaved by membrane type 1 matrixmetalloproteinase (MT-MMP); HGPEGLRVGFYESDVMGRGHAR-LVHVEEPHT (SEQ ID NO:32) cleaved by stromelysin 3 (or MMP-11), thermolysin, fibroblast collagenase and stromelysin-1; GPQGLAGQRGIV (SEQ ID NO:33) cleaved by matrix metalloproteinase 13 (collagenase-3); GGSGQRGRKALE (SEQ ID NO:34) cleaved by tissue-type plasminogen activator (tPA); SLSALLSSDIFN (SEQ ID NO:35) cleaved by human prostate-specific antigen; SLPRFKIIGGFN (SEQ ID NO:36) cleaved by kallikrein (hK3); SLLGIAVPGNFN (SEQ ID NO:37) cleaved by neutrophil elastase; and FFKNIVTPRTPP (SEQ ID NO:38) cleaved by calpain (calcium activated neutral protease).; and CQPQGLAKC (SEQ ID NO:39) cleaved by matrix metalloproteinase 13. In specific embodiments, the proteolytically cleavable cross-linker polypeptide can be cleaved by a matrix metalloproteinase (MMP). In specific embodiments, the proteolytically cleavable cross-linker polypeptide can be cleaved by MMP-13. In specific embodiments, the proteolytically cleavable cross-linker polypeptide includes the amino acid sequence CQPQGLAKC (SEQ ID NO:39).

A cross-linker can be present at any convenient concentration. In some cases, a cross-linker is present at a concentration in a range of from 0.5 mg/ml to 50 mg/ml (e.g., 0.5 mg/ml to 30 mg/ml, 0.5 mg/ml to 25 mg/ml, 0.5 mg/ml to 20 mg/ml, 0.5 mg/ml to 15 mg/ml, 0.5 mg/ml to 10 mg/ml, 1 mg/ml to 10 mg/ml, 1 mg/ml to 7.5 mg/ml, 1 mg/ml to 5 mg/ml, 2 mg/ml to 4 mg/ml, or 3 mg/ml).

Cells

In some embodiments, cells are embedded within a subject hydrogel. Suitable cells are brown adipocytes or any cell that can become (e.g., differentiate into) a brown adipocyte. Exemplary cells to be embedded in a subject hydrogel include, but are not limited to: brown adipocytes, brown adipocyte pre-cursor cells, adipose precursor cells (pre-adipocytes), and adipose derived mesenchymal stem cells (ADMSCs).

Adipose Derived Mesenchymal Stem Cells (ADMSCs)

The term "adipose derived mesenchymal stem cell" or "ADMSC" refers to the multi-potent stem cells found in the adipose tissue of post-natal mammals. ADMSCs are also referred to in the literature as adipose-derived adult stem (ADAS) cells, adipose-derived adult stromal cells, adipose-derived stromal cells (ADSCs), adipose stromal cells (ASCs), adipose mesenchymal stem cells (AdMSCs), lipoblast, pericyte, preadipocyte, and processed lipoaspirate (PLA) cells. The International Fat Applied Technology Society (IFATS) reached a consensus to adopt the term "adipose-derived stem cells" (ASCs) to identify the isolated, plastic-adherent, multipotent cell population.

The above terms generally refer to mesenchymal stem cells isolated from white adipose tissue. However, it is envisioned herein that mesenchymal stem cells may also be derived from any adipose tissue (e.g., brown adipose tissue (BAT)). Thus, the above terms (e.g., "ADMSC", "ASC", etc.) as used herein encompass adipose derived mesenchymal stem cells from any adipose tissue (e.g., WAT, BAT, and the like).

The term "white adipose tissue derived mesenchymal stem cells" (WAT-MSCs) as used herein refers to the same cell type as the term ADMSC, except that the term WAT-MSCs refers specifically to stem cells derived from white adipose tissue and excludes stem cells derived from brown adipose tissue. Thus, the term ADMSC encompasses the term WAT-MSCs. Cells suitable for the compositions and methods disclosed herein include ADMSCs and/or WAT-MSCs.

ADMSCs have the potential to differentiate into a variety of cell types including but not limited to cells of osteogenic, adipogenic, and chondrogenic lineages. In contrast to cell lines, ADMSCs have not undergone immortalization. A number of scientific publications have described the underlying biology of ADMSCs, preclinical studies for the use of ADMSCs in regenerative medicine in various fields have been performed, and the efficacy of ADMSCs has been determined in several clinical trials.

ADMSCs for use in the subject methods can be isolated by any convenient method (e.g., from subcutaneous and/or visceral adipose tissue, from an adipose depot, etc.). Subcutaneous adipose tissue samples can be obtained under local anesthesia. Methods used for isolating ADMSCs may include collagenase digestion followed by centrifugal separation to isolate the Stromal Vascular Fraction from mature adipocytes.

As a non-limiting example, to isolate ADMSCs, adipose tissue obtained as excised surgical specimens (e.g., a biopsy, a lipoaspirate from liposuction, etc.) can be digested with a collagenase enzyme (e.g., a bacterially-derived collagenase) in the presence of calcium to release the individual cell components. Subsequently, mature adipocytes can be separated (e.g., via differential centrifugation), from the remaining cells, which form a Stromal Vascular Fraction (SVF) pellet. The SVF cell population includes endothelial cells, fibroblasts, B and T-lymphocytes, macrophages, myeloid cells, pericytes, pre-adipocytes, smooth muscle cells, and the culture adherent ADMSCs.

Culture of SVF cells under standard conditions on an adherent surface eventually (within the first few passages) results in the appearance of a relatively homogeneous population of ADMSCs, which are adherent mesenchymal stem cells. ADMSCs display a fibroblast-like morphology and lack the intercellular lipid droplets seen in adipocytes. ADMSCs can be verified, for example, by demonstrating that the cells can differentiate into multiple different lineages (e.g., adipocytes can be identified using, for example, Oil Red O stain; osteoblasts can be identified using, for example, Alizarin Red stain; and chondrocytes can be identified using, for example, Alcian Blue stain). Protein and nucleic acid markers can also be used to verify differentiation into multiple lineages.

Thus, the isolation of ADMSCs from a lipoaspirate can include: (1) wash the lipoaspriate in buffered saline solution; (2) subject the lipoaspirate to collagenase digestion; (3) centrifuge and isolate the stromal vascular fraction (SVF) pellet; (4) culture the heterogeneous SVF cells on an adherent surface; (5) isolate adherent ADMSCs; and optionally (6) verify the that the isolated cells are ADMSCs.

After culturing SVF (e.g., 2 to 6 days, any convenient culture medium can be used), a single milliliter of human lipoaspirate can yield between 0.25 to $0.375 \times 10^6$ ADMSCs capable of differentiating along the adipogenic (adipocyte), chondrogenic (chondrocyte), and osteogenic (osteoblast) lineages in vitro.

If desired, isolated ADMSCs can be expanded in monolayer culture on standard tissue culture plastics with a basal medium (e.g., in some cases containing 10% fetal bovine serum). Since liposuction from a single patient can result in >1 L of tissue, it is feasible to generate hundreds of millions of ADMSCs from an individual within a single in vitro cell culture passage. In contrast to the mixed cell population of the SVF, ADMSCs are relatively homogeneous (e.g., based on their expression profile of surface antigens).

The International Society for Cellular Therapy (ISCT) and IFATS have established minimal criteria defining SVF cells and ASC (ADMSCs) based on functional and quantitative criteria. The four criteria used herein are: (1) ADMSCs are plastic-adherent when maintained under standard culture conditions; (2) ADMSCs have the capacity for osteogenic, adipogenic, and chondrogenic differentiation; (3) ADMSCs express the markers (i.e., molecular markers) CD29, CD34, CD36, CD49f, CD73, CD90 (Thy-1), CD105, CD133, c-kit, and c-met; and (4) ADMSCs are negative for CD45, CD106, and CD31. The adipocytic, chondroblastic and osteoblastic differentiation assays (e.g., Oil Red O stain, Alcian blue stain, and Alizarin red stain, respectively) can be used to assess potency and differentiation capacity, and can be used in conjunction with a quantitative evaluation of differentiation either biochemically or by reverse transcription polymerase chain reaction (RT-PCR). The colony-forming unit—fibroblast (CFU-F) assay is recommended by the IFATS to calculate population doublings capacity of ADMSCs.

For more information regarding the nature of ADMSCs, including the isolation and culture of ADMSCs, see (i) Gimble et al., Circ Res. 2007 May 11; 100(9):1249-60:

"Adipose-derived stem cells for regenerative medicine"; (ii) Gimble et al., Organogenesis. 2013 Jan. 1; 9(1): "Adipose-derived stromal/stem cells: A primer"; (iii) Bourin et al, Cytotherapy. 2013 June; 15(6):641-8: "Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT)"; (iv) Gentile et al, Stem Cells Transl Med. 2012 March; 1(3):230-6: "Concise review: adipose-derived stromal vascular fraction cells and platelet-rich plasma: basic and clinical implications for tissue engineering therapies in regenerative surgery"; and (v) Mizuno et al., Stem Cells. 2012 May; 30(5):804-10: "Concise review: Adipose-derived stem cells as a novel tool for future regenerative medicine"; all of which are hereby incorporated by reference in their entirety.

A cell population that includes ADMSCs (e.g., a population of cells from liposuction) can be enriched for ADMSCs (e.g., via flow cytometry) using ADMSC cell surface markers (e.g., CD29, CD34, CD36, CD49f, CD73, CD90 (Thy-1), CD105, CD133, c-kit, c-met, and the like). In some cases, a cell population that includes ADMSCs (e.g., a population of cells from liposuction) can be enriched (e.g., via flow cytometry) for cells that differentiate into brown adipocytes. For example, to enrich for a subpopulation of ADMSCs that differentiate into brown adipocytes, a cell population that includes ADMSCs can be enriched using cell surface markers (e.g., Sca-1 (+), CD24, CD29, CD137, and the like).

Methods

Aspects of the disclosure include methods of inducing cells (e.g., ADMSCs) to differentiate into brown adipocytes, and methods of increasing the number of brown adipocytes in an individual. In some embodiments, cells are cultured (contacted with growth medium).

Cell Culture Components

Standard cell culture components that are suitable for inclusion in a subject cell culture composition include, but are not limited, to, a vitamin; an amino acid (e.g., an essential amino acid); a pH buffering agent; a salt; an antimicrobial agent (e.g., an antibacterial agent, and antimycotic agent, etc.); serum; an energy source (e.g., a sugar); a nucleoside; a lipid; trace metals; a cytokine, a growth factor, a stimulatory factor, and the like. Any convenient cell culture media can be used, and as is known in the art, various cell types grow better in particular media preparations (in some cases, particular media formulations have been optimized to culture specific types of cells (e.g., neurons, cardiomyocytes, hepatocytes, etc.). Accordingly, any convenient cell culture media can be used and may be tailored to the particular cell type being cultured.

The major ions and their concentrations in cell culture media are generally present in standard, commercially available, liquid culture media (e.g., basal liquid culture media). Most standard types of media (e.g., DMEM, DMEM/F12. BME, RPM 1640, and the like) use relatively narrow and fixed ranges for the concentrations of bulk ions in general and the monovalent cations Na$^+$ and K$^+$ in particular. This is in line with the fact that the ionic balance of the bulk ions in general and the monovalent cations Na$^+$ and K$^+$ in particular is a rather universal property of almost all mammalian cells. Any convenient media that can be used to culture cells in vitro is suitable for use with the subject compositions and methods.

In accordance with the typical concentration of sodium ions inside and outside a generic mammalian cell (Alberts et al., Molecular Biology of the Cell (1994)) mostly sodium concentrations of about 145 mM are chosen together with potassium ion concentrations of around 5 mM. For most media types this results in a ratio between sodium and potassium ions that ranges between about 20-30 (see U.S. Pat. No. 5,135,866; and US Patent Publication No. 2013/0122543, both of which are hereby incorporated by reference in their entirety).

The osmolality of the media at the beginning of culturing is typically between about 280 and about 365 mOsm, but may also gradually increase during culturing and the addition of feeding solutions to values of less than or about 600 mOsm/kg. A cell culture composition of the present disclosure can have an initial osmolality in a range of from about 200 to about 400 mOsm/kg (e.g., from about 200 to about 400 mOsm/kg, from about 250 to about 375 mOsm/kg, or from about 275 to about 350 mOsm/kg).

In some embodiments, a subject cell culture medium includes animal serum (e.g., fetal bovine serum (FBS); bovine serum, chicken serum, newborn calf serum, rabbit serum, goat serum, normal goat serum (NGS); horse serum; lamb serum, porcine serum, and the like). A wide range of serum concentrations can be used. A cell culture composition of the present disclosure can have a concentration of serum in a range of from 1% to 50% (e.g., from 2% to 40%, from 2% to 30%, from 2% to 25%, from 2% to 20%, from 2% to 15%, from 2% to 10%, from 2% to 7%, from 2% to 5%, from 3% to 12%, from 5% to 15%, from 8% to 12%, from 9% to 11%, from 8% to 20%, 5%, 6%, 7%, 8%, 9%, 10%, 11%, 12%, 13%, 14%, or 15%). In some embodiments, a subject cell culture medium is serum free. Serum comprises growth factors and in many cases, is it unknown exactly which growth factors, or exactly how many growth factors are present in any given serum. In some cases, at least one of the growth factors present in a serum is known.

In some cases, a subject cell culture composition includes a conditioned medium (e.g., in some cases, a subject cell culture composition includes compounds (e.g., proteins, chemicals, etc.) that were secreted into the medium by cultured cells A cell culture composition of the present disclosure can have a pH in a range of from about 6.8 to about 7.4, e.g., 6.8 to 7.0, 7.0 to 7.2, or 7.2 to about 7.4.

In some embodiments, cells (e.g., ADMSCs) are cultured in (i.e., contacted with) basal differentiation medium (BDM) and/or maintenance medium (MM).

Basal differentiation medium (BDM) can include:
(i) basal liquid culture media (e.g., DMEM);
(ii) Insulin (e.g., at a concentration in a range of from 0.5 µM to 1.5 µM (e.g., from 0.6 µM to 1.4 µM, from 0.6 µM to 1.2 µM, from 0.6 µM to 1.1 µM, from 0.7 µM to 1 µM, from 0.8 µM to 0.9 µM, or 0.85 µM));
(iii) Triiodothyronine (T3) (e.g., at a concentration in a range of from 5 nM to 15 nM (e.g., from 7.5 nM to 12.5 nM, from 8 nM to 12 nM, from 9 nM to 11 nM, or 10 nM));
(iv) Dexamethasone (Dex) (e.g., at a concentration in a range of from 0.5 µM to 1.5 µM (e.g., from 0.75 µM to 1.25 µM, from 0.8 µM to 1.2 µM, from 0.9 µM to 1.1 µM, or 1 µM));
(v) Isobutylmethylxanthine (IBMX) (e.g., at a concentration in a range of from 200 µM to 800 µM (e.g., from 300 µM to 700 µM, from 400 µM to 600 µM, from 450 µM to 550 µM, or 500 µM)); and/or
(vi) serum (e.g., 10% fetal bovine serum (FBS)).

In some cases, BDM does not contain serum. In some cases, BDM does not contain non-human serum (e.g., does not contain item (vi) above, contains a convenient substitute(s) for serum, etc.).

Maintenance medium (MM) can include
(i) basal liquid culture media (e.g., DMEM);
(ii) Insulin (e.g., at a concentration in a range of from 0.5 µM to 1.5 µM (e.g., from 0.6 µM to 1.4 µM, from 0.6 µM to 1.2 µM, from 0.6 µM to 1.1 µM, from 0.7 µM to 1 µM, from 0.8 µM to 0.9 µM, or 0.85 µM));
(iii) 100 nM Rosiglitazone (e.g., at a concentration in a range of from 50 nM to 200 nM (e.g., from 50 nM to 150 nM, from 75 nM to 150 nM, from 75 nM to 125 nM, from 80 nM to 120 nM, from 90 nM to 110 nM, from 95 nM to 105 nM, or 100 nM); and
(iv) serum (e.g, 10% fetal bovine serum (FBS)).

In some cases, MM does not contain serum. In some cases, MM does not contain non-human serum (e.g., does not contain item (iv) above, contains a convenient substitute(s) for serum, etc.).

Methods of Inducing Cells to Differentiate into Brown Adipocytes

Aspects of the disclosure include inducing cells to differentiate into brown adipocytes. Cells can be contacted with (i.e., cultured with) any suitable culture medium (e.g., basal liquid culture medium, BDM, MM, etc.). A cell (e.g., an ADMSC, a pre-adipocyte, a BDM-contacted cell, etc.) can be cultured in the presence and/or absence of hydrogel. In some cases, a cell is cultured in the absence of hydrogel for a period of time and in the presence of hydrogel for a period of time. When cultured in the presence of hydrogel, a cell can be mixed with the polymer network of the hydrogel in a liquid state (e.g., prior to gelation) and then gelation can occur after mixing (e.g., prior to culturing for a period of time or prior to culturing for a period of time). Culturing can occur in the liquid state and/or the gel state. In some cases, the hydrogel is in a gel state prior to mixing with cells and cells can penetrate the gel to incorporate and embed within the gel.

In some embodiments, cells (e.g., ADMSCs, WAT-MSCs, pre-adipocytes, etc.) are cultured in (i.e., contacted with) basal differentiation medium (BDM). In some embodiments, ADMSCs are contacted with BDM for a period of time in a range of from 1 day to 7 days (e.g., 1 day to 7 days, 1 day to 6 days, 1 day to 5 days, 1 day to 4 days, 1 day to 3 days, 2 days to 7 days, 2 days to 6 day, 2 days to 5 days, 2 days to 4 days, 2 days to 3 days, 3 days to 7 days, 3 days to 6 days, 3 days to 5 days, 3 days to 4 days, 1 day, 2 days, 3 days, 4 days, 5 days, 6 days, or 7 days) (e.g., to induce differentiation), thereby generating a BDM-contacted cell population. In some embodiments, ADMSCs are contacted with BDM for 1 day or more (e.g., 2 days or more, 3 days or more, 4 days or more, 5 days or more, 6 days or more, or 7 days or more) (e.g., to induce differentiation), thereby generating a BDM-contacted cell population. In some cases, BDM-contacted cells are mixed with a subject hydrogel.

In some embodiments, cells (e.g., cells of a BDM-contacted cell population (e.g., either in the absence of hydrogel, or in the presence of hydrogel, e.g., after being mixed with hydrogel) are cultured in (i.e., contacted with) maintenance medium (MM) (can be in the presence or absence of hydrogel). In some cases, cells of a BDM-contacted cell population are contacted with MM for a period of time in a range of from 1 day to 14 days in maintenance medium (MM) (e.g., 2 days to 14 days, 3 days to 14 days, 4 days to 14 days, 5 days to 14 days, 6 days to 14 days, 7 days to 14 days, 8 days to 14 days, 9 days to 14 days, 10 days to 14 days, 10 days to 13 days, or 11 days to 13 days) to complete differentiation into UCP1 expressing adipocytes (i.e., brown adipocytes). In some cases, cells (e.g., cells of a BDM-contacted cell population) are contacted with MM for 1 day or more (e.g., 2 days or more, 3 days or more, 4 days or more, 5 days or more, 6 days or more, 7 days or more, 8 days or more, 9 days or more, 10 days or more, 11 days or more, 12 days or more, 13 days or more, or 14 days or more) to complete differentiation.

In some embodiments, the number of cells (e.g., ADM-SCs, WAT-MSCs, BDM-contacted cells, brown adipocytes, or a combination thereof) embedded within the hydrogel is in a range of from $1\times10^5$ cells to $1\times10^{10}$ cells (e.g., $1.5\times10^5$ cells to $1\times10^9$ cells, $1\times10^5$ cells to $1\times10^8$ cells, $1\times10^5$ cells to $1\times10^7$ cells, $1\times10^5$ cells to $1\times10^6$ cells, $1.5\times10^5$ cells to $1\times10^6$ cells, $2\times10^5$ cells to $5\times10^5$ cells, $4\times10^7$ cells to $1\times10^{10}$ cells, $1\times10^8$ cells to $1\times10^{10}$ cells, $1\times10^8$ cells to $5\times10^9$ cells, $3.5\times10^8$ cells to $5\times10^9$ cells, $4\times10^8$ cells to $2\times10^9$ cells, or $4\times10^8$ cells to $1\times10^9$ cells).

In some embodiments, the number of cells (e.g., ADM-SCs, WAT-MSCs, BDM-contacted cells, brown adipocytes, or a combination thereof) embedded within the hydrogel is $1\times10^5$ or more cells (e.g., $1.5\times10^5$ or more, $2\times10^5$ or more, $2.5\times10^5$ or more, $3\times10^5$ or more, $3.5\times10^5$ or more, $4\times10^5$ or more, $4.5\times10^5$ or more, $5\times10^5$ or more, $5.5\times10^5$ or more, $6\times10^5$ or more, $5\times10^7$ or more, $1\times10^8$ or more, $1.5\times10^8$ or more, $2\times10^8$ or more, $2.5\times10^8$ or more, $3\times10^8$ or more, $3.5\times10^8$ or more, $4\times10^8$ or more, $4.5\times10^8$ or more, $5\times10^8$ or more, $5.5\times10^8$ or more, $6\times10^8$ or more, $7\times10^8$ or more, or $1\times10^9$ or more).

In some embodiments, the concentration of cells (e.g., cells per ml of hyrdogel) (e.g., ADMSCs, WAT-MSCs, BDM-contacted cells, brown adipocytes, or a combination thereof) embedded within the hydrogel is in a range of from $1\times10^5$ cells/ml to $1\times10^8$ cells/ml (e.g., $5\times10^5$ cells/ml to $5\times10^7$ cells/ml, $5\times10^5$ cells/ml to $1\times10^7$ cells/ml, $1\times10^6$ cells/ml to $1\times10^7$ cells/ml, $1\times10^6$ cells/ml to $7\times10^6$ cells/ml, or $2\times10^6$ cells/ml to $5\times10^6$ cells/ml).

In some embodiments, the concentration of cells (e.g., cells per ml of hyrdogel) (e.g., ADMSCs, WAT-MSCs, BDM-contacted cells, brown adipocytes, or a combination thereof) embedded within the hydrogel is $1\times10^5$ cells/ml or more (e.g., $1\times10^5$ cells/ml or more, $2\times10^5$ cells/ml or more, $3\times10^5$ cells/ml or more, $4\times10^5$ cells/ml or more, $5\times10^5$ cells/ml or more, $6\times10^5$ cells/ml or more, $7\times10^5$ cells/ml or more, $8\times10^5$ cells/ml or more, $9\times10^5$ cells/ml or more, $1\times10^6$ cells/ml or more, $2\times10^6$ cells/ml or more, $3\times10^6$ cells/ml or more, $4\times10^6$ cells/ml or more, $5\times10^6$ cells/ml or more, $6\times10^6$ cells/ml or more, $7\times10^6$ cells/ml or more, or $8\times10^6$ cells/ml or more).

In some embodiments, methods of inducing differentiation (e.g., into brown adipocytes) include introducing (i.e., implanting) a subject composition (e.g., having brown adipocytes) into an individual (described in more detail below). In some cases, cells to be implanted (e.g., ADMCs) are from the individual (i.e., the cells are autologous). In some cases, the ADMSCs are obtained from a donor individual other than the prospective recipient (i.e., the cells are non-autologous), where the donor and the prospective recipient are of the same species (e.g., where the donor and the prospective recipient are both humans). In some cases, a subject method includes obtaining cells (e.g., ADMSCs, WAT-MSCs, etc.) from the individual. In some cases, obtaining cells from an individual includes liposuction. Liposuction can be performed from any convenient body location (e.g., abdomen, breast tissue (male or female), hips, outer thighs, flanks, back, inner thighs, inner knees, upper arms, submental (e.g., chin, gullet, etc.), and the like. In some cases, a subject composition does not include cells (i.e., is cell free).

In some cases, a cell-free composition is implanted into an individual and cells of the individual (e.g., naturally present ADMSCs, stems cells, mesenchymal stem cells (MSCs), etc.) are induced to differentiate (in vivo) into brown adipocytes.

Verifying the Presence of Brown Adipocytes

In some cases, a subject method includes a step of verifying the presence of brown adipocytes. For example, in some cases, ADMSCs differentiate into brown adipocytes while associated with a hydrogel. In some such cases (e.g., prior to implanting the hydrogel into an individual), a step of verifying that brown adipocytes are present in the hydrogel composition is performed.

Verification can be performed using any convenient method. Various features that can be included in a verification step include, but are not limited to: glucose/fatty acid uptake rate, lipid accumulation, cell morphology, mitochondrial number, and cellular respiration rate. Once suitable method for verifying the presence of brown adipocytes is visual inspection (e.g., via a microscope). Brown fat cells (brown adipocytes) are multilocular cells with lipid droplets scattered throughout the cytoplasm. The brown color is caused by a large number of mitochondria present in these cells (e.g., brown adipocytes have an extensive mitochondrial network). Thus, mitochondrial dyes can be used to distinguish brown from white adipocytes. On the other hand, white fat cells (white adipocytes) are unilocular cells that contain a large lipid droplet surrounded by a layer of cytoplasm.

Glucose/fatty acid uptake rates, lipid accumulation and cell morphology: The ability of brown adipocytes to uptake glucose and fatty acid substrates is directly related to basic metabolic rate and caloric consumption. Thus, any convenient method for detecting and/or measuring fatty acid uptake and/or lipid accumulation can be used. For example, radio- and/or fluorescently-labeled 2-deoxyglucose and/or long chain fatty acids can be used to determine cellular uptake rates (e.g., as described in Stahl lab78, which is hereby incorporated by reference in its entirety). Lipid accumulation and cell morphology are also suitable for be assessing whether a cell is a brown adipocyte. Any convenient method can be used. For example, neutral lipid dyes such as BODIPY and/or Oil RedO can be used to measure lipid accumulation in cells. Cell and tissue morphology can be determined using standard cell histology stains (e.g., H&E, Masson's Trichrome, and the like).

Mitochondrial number and cellular respiration rates: Additional criteria for verification include mitochondrial numbers, and the ability of brown adipocytes to effectively channel metabolic substrates into uncoupled mitochondrial respiration. Mitochondrial numbers can be measured, for example, by staining cells with mitochondrial dyes (visual inspection); assaying for activity and/or expression levels (e.g., measuring protein levels and/or mRNA levels) of markers such as UCP1, complex IV, and cytochrome (C, C1, B, and/or A) in isolated mitochondria. Both Clark-type as well as solid state sensor (Seahorse Respirometer) based respirometers can be used to measure GOP state 4, palmitate state 3, and FCCP uncoupled state 3 respiration and to perform mitochondrial "stress tests", which can be used to determine/measure a cell's (and/or cells of a cell population) basal and/or uncoupled (FCCP) respiration rate. Brown adipocytes have a higher basal and uncoupled respiration rate than undifferentiated MSCs (ADMSCs, BSM-contacted cells, WAT-MSCs, etc.). Experiments can be performed with and without the addition of a β-adrenergic agonist (e.g., CL 316,243), which induces increased cellular respiration in brown adipocytes.

Biomarkers: Biomarker analysis can be used to determine the presence or absence (e.g., determining the percentage of) brown adipocytes in a cell population. The term "biomarker" as used herein means a gene product (i.e. protein or RNA), whose concentration (i.e., "level") indicates whether a cell is of a particular cell type (e.g., brown adipocyte, white adipocyte, ADMSC, etc.). For example, as used herein, a biomarker whose level is higher (i.e., is enriched) in brown adipocytes relative to ADMSCs and/or white adipocytes is a "brown fat biomarker", and a biomarker whose level is higher in white adipocytes relative to ADMSCs and/or brown adipocytes is a "white fat biomarker".

In some cases, the level of a brown fat biomarker is 1.5-fold or more higher in a brown adipocyte than an ADMSC and/or a white adipocyte (e.g., 2-fold or more higher, 2.5-fold or more higher, 3-fold or more higher, 3.5-fold or more higher, 4-fold or more higher, 4.5-fold or more higher, or 5-fold or more higher, 8-fold or more higher, 10-fold or more higher, etc.). Thus, a brown adipocyte should exhibit an increased expression level of at least one brown fat biomarker relative to a control cell (e.g., an ADMSC, a white adipocyte, a pre-adipocyte, etc.).

In some cases, the level of a white fat biomarker is 1.5-fold or more higher in a white adipocyte than an ADMSC and/or a brown adipocyte (e.g., 2-fold or more higher, 2.5-fold or more higher, 3-fold or more higher, 3.5-fold or more higher, 4-fold or more higher, 4.5-fold or more higher, or 5-fold or more higher, 8-fold or more higher, 10-fold or more higher, etc.). Thus, a brown adipocyte should have no detectable expression, or at least reduced expression of a white fat biomarker relative to a white adipocyte.

Exemplary suitable brown fat biomarkers and white fat biomarkers are presented in Table 3. For example, UCP1 (uncoupling protein 1 (mitochondrial, proton carrier)) can be utilized as a brown fat biomarker. UCP1 is also known as UCP and SLC25A7. An exemplary cDNA sequence of an mRNA encoding UCP1 is:

(SEQ ID NO: 40)
AGAGCAAGGGAAAGGAACTTCCTCCACCTTCGGGGCTGGAGCCCTTT

TCCTCTGCATCTCCAGTCTCTGAGTGAAGATGGGGGCCTGACAGCC

TCGGACGTACACCCGACCCTGGGGGTCCAGCTCTTCTCAGCTGGAAT

AGCGGCGTGCTTGGCGGACGTGATCACCTTCCCGCTGGACACGGCCA

AAGTCCGGCTCCAGGTCCAAGGTGAATGCCCGACGTCCAGTGTTATT

AGGTATAAAGGTGTCCTGGGAACAATCACCGCTGTGGTAAAAACAGA

AGGGCGGATGAAACTCTACAGCGGGCTGCCTGCGGGGCTTCAGCGGC

AAATCAGCTCCGCCTCTCTCAGGATCGGCCTCTACGACACGGTCCAG

GAGTTCCTCACCGCAGGGAAAGAAACAGCACCTAGTTTAGGAAGCAA

GATTTTAGCTGGTCTAACGACTGGAGGAGTGGCAGTATTCATTGGGC

AACCCACAGAGGTCGTGAAAGTCAGACTTCAAGCACAGAGCCATCTC

CACGGAATCAAACCTCGCTACACGGGGACTTATAATGCGTACAGAAT

AATAGCAACAACCGAAGGCTTGACGGGTCTTTGGAAAGGGACTACTC

CCAATCTGATGAGAAGTGTCATCATCAATTGTACAGAGCTAGTAACA

TATGATCTAATGAAGGAGGCCTTTGTGAAAAACAACATATTAGCAGA

TGACGTCCCCTGCCACTTGGTGTCGGCTCTTATCGCTGGATTTTGCG

CAACAGCTATGTCCTCCCCGGTGGATGTAGTAAAAACCAGATTTATT

AATTCTCCACCAGGACAGTACAAAAGTGTGCCCAACTGTGCAATGAA

-continued

```
AGTGTTCACTAACGAAGGACCAACGGCTTTCTTCAAGGGGTTGGTAC

CTTCCTTCTTGCGACTTGGATCCTGGAACGTCATTATGTTTGTGTGC

TTTGAACAACTGAAACGAGAACTGTCAAAGTCAAGGCAGACTATGGA

CTGTGCCACATAA.
```

An exemplary amino acid sequence of a UCP1 protein is:

```
                                         (SEQ ID NO: 41)
MGGLTASDVHPTLGVQLFSAGIAACLADVITFPLDTAKVRLQVQGEC

PTSSVIRYKGVLGTITAVVKTEGRMKLYSGLPAGLQRQISSASLRIG

LYDTVQEFLTAGKETAPSLGSKILAGLTTGGVAVFIGQPTEVVKVRL

QAQSHLHGIKPRYTGTYNAYRIIATTEGLTGLWKGTTPNLMRSVIIN

CTELVTYDLMKEAFVKNNILADDVPCHLVSALIAGFCATAMSSPVDV

VKTRFINSPPGQYKSVPNCAMKVFTNEGPTAFFKGLVPSFLRLGSWN

VIMFVCFEQLKRELSKSRQTMDCAT.
``` but are not limited to: fluorescent antibody staining, immunohistochemistry, enzyme linked immunosorbent assay (ELISA), Western blotting, proteomic arrays, xMAPTM microsphere technology (e.g., Luminex technology), flow cytometry, mass spectrometry, and the like.

Suitable methods for assaying RNA levels include, but are not limited to: hybridization-based methods (e.g., Northern blotting, array hybridization (e.g., microarray); in situ hybridization; in situ hybridization followed by FACS; and the like)(Parker & Barnes, Methods in Molecular Biology 106:247-283 (1999)); RNAse protection assays (Hod, Biotechniques 13:852-854 (1992)); polymerase chain reaction (PCR)-based methods (e.g., reverse transcription PCR (RT-PCR), semi-quantitative RT-PCR, quantitative RT-PCR (qRT-PCR), real-time RT-PCR, etc.) (Weis et al., Trends in Genetics 8:263-264 (1992)); nucleic acid sequencing methods (e.g., Sanger sequencing, next generation sequencing (i.e., massive parallel high throughput sequencing, e.g., Illumina's reversible terminator method, Roche's pyrosequencing method (454), Life Technologies' sequencing by ligation (the SOLiD platform), Life Technologies' Ion Torrent platform, single molecule sequencing, etc.)); and the like.

TABLE 3

Brown fat biomarkers and white fat biomarkers

| Factor name | Also known as | Sequence identifiers (cDNA and protein) (including isoforms) |
|---|---|---|
| Brown fat biomarkers | | |
| UCP1 | uncoupling protein 1 (mitochondrial, proton carrier | SEQ ID NOs: 40, 41 |
| PRDM16 | PR domain containing 16 | NM_022114.3; NM_199454.2 NP_071397.3; NP_955533.2 |
| CYC1 | cytochrome c-1 | NM_001916.3; NP_001907.2 |
| ELOVL3 | ELOVL fatty acid elongase 3 | NM_152310.2; NP_689523.1 |
| COX8A | cytochrome c oxidase subunit VIIIA (ubiquitous) | NM_004074.2; NP_004065.1 |
| DIO2 | deiodinase, iodothyronine, type II | NM_000793.5; NP_000784.2 NM_001007023.3; NP_001007024.1 NM_001242502.1; NP_001229431.1 NM_001242503.1; NP_001229432.1 NM_013989.4; NP_054644.1 |
| PGC-1α | PPARGC1A; peroxisome proliferator-activated receptor gamma, coactivator 1 alpha | NM_013261.3; NP_037393.1 |
| Cidea | cell death-inducing DFFA-like effector a | NM_001279.3; NP_001270.1 |
| Cox7a1 | cytochrome c oxidase subunit VIIa polypeptide 1 (muscle) | NM_001864.2; NP_001855.1 |
| FGF21 | fibroblast growth factor 21 | NM_019113.2; NP_061986.1 |
| CEBPB | C/ebpβ; CCAAT/enhancer binding protein (C/EBP), beta | NM_001285878.1; NP_001272807.1 NM_001285879.1; NP_001272808.1 NM_005194.3; NP_005185.2 |
| ap2 | FABP4; fatty acid binding protein 4 | NM_001442.2; NP_001433.1 |
| White fat biomarkers | | |
| RETN | Resistin | NM_001193374.1; NP_001180303.1 NM_020415.3; NP_065148.1 |
| AGT | Angiotensinogen; serpin peptidase inhibitor, clade A, member 8 | NM_000029.3; NP_000020.1 |
| Chemerin | RARRES2; retinoic acid receptor responder (tazarotene induced) 2 | NM_002889.3; NP_002880.1 |
| Pank3 | pantothenate kinase 3 | NM_024594.3; NP_078870.1 |
| LEP | leptin | NM_000230.2; NP_000221.1 |
| ALDH1A1 | aldehyde dehydrogenase 1 family, member A1 | NM_000689.4; NP_000680.2 |
| DPT | dermatopontin | NM_001937.4; NP_001928.2 |
| INHBB | inhibin, beta B | NM_002193.2; NP_002184.2 |

Any convenient method of assaying (e.g., measuring) the expression level of a biomarker (protein and/or RNA) can be used. Suitable methods for assaying protein levels include, Any convenient method of verifying can be used to determine whether a component (e.g., an enhancement compound, a cell adhesion ligand, etc.) enhances the differentiation of cells (e.g., adipose derived mesenchymal stem cells (ADMSCs)) into brown adipocytes. For example, experiments can be performed to differentiate a cell (e.g., an ADMSC, a WAT-MSC, and the like) into a brown adipocyte in the presence and absence of the candidate component. Those candidate components that result in an increased percentage of brown adipocytes (relative to the percentage of brown adipocytes when differentiated in the absence of the component) can be considered to enhance the differentiation of the cell type tested (e.g., ADMSC) into a brown adipocyte.

Likewise, any convenient method of verifying can be used to determine whether a component (e.g., an enhancement compound, a cell adhesion ligand, etc.) enhances the maintenance of brown adipocytes. The term "maintenance of brown adipocytes" as used herein refers to the ability of a component to maintain the identity and/or function of a brown adipocyte. For example, brown adipocytes from a population of brown adipocytes may die over time, may exhibit decreased cell proliferation, may lose cell identity (e.g., regress to a less differentiated state, e.g., towards an ADMSC), may exhibit reduced function, and the like. Thus, a candidate component (e.g., an enhancement compound, a cell adhesion ligand, etc.) can be said to enhance the maintenance of brown adipocytes when, compared to the absence of the candidate component, the presence of the candidate component: (i) increases the presence of brown adipocytes (e.g., increases the percentage of brown adipocytes in a population, increases the overall number of brown adipocytes, etc.), e.g., by increasing survival of brown adipocytes, by reducing death of brown adipocytes, by allowing brown adipocytes to maintain cell identity, and the like; and/or (ii) increases the function of brown adipocytes (e.g., by increasing the ability of brown adipocytes to take up glucose and/or fatty acids, by increasing the ability of brown adipocytes to accumulate lipids, by increasing the number of mitochondria in brown adipocytes, by increasing the cellular respiration rate of brown adipocytes, and the like).

Increasing the Number of Brown Adipocytes in an Individual

Aspects of the disclosure include methods of increasing the number of brown adipocytes in an individual. A method of increasing the number of brown adipocytes in an individual includes the step of implanting (e.g., injecting, surgically implanting, etc.) a subject composition (e.g., without cells; with cells that are embedded within a hydrogel, e.g., brown adipocytes, ADMSCs, WAT-MSCs, etc.; with cells that are pre-mixed with a hydrogel in liquid state; and the like).

In some cases, cells are cultured (i.e., contacted with a suitable culture medium) for a period of time prior to implantation. In some cases, cells are implanted before beginning the differentiation process (e.g., implanted as ADMSCs, implanted as WAT-MSCs, and the like). In some cases, the cells begin the differentiation process (i.e., are induced to differentiate) (e.g., by contacting cells with a basal differentiation medium (BDM)) prior to implantation. In some cases, cells are implanted into an individual prior to completing the differentiation process toward becoming a brown adipocyte. In some cases, cells complete differentiation into brown adipocytes after being implanted (i.e., they complete the differentiation process in vivo). In some cases, cells differentiate into brown adipocytes prior to implantation (i.e., the cells are implanted as brown adipocytes).

Cells can be contacted with (i.e., cultured with) any suitable culture medium (e.g., basal liquid culture medium, BDM, MM, etc.). A cell (e.g., an ADMSC, a pre-adipocyte, a BDM-contacted cell, etc.) can be cultured in the presence and/or absence of hydrogel. In some cases, a cell is cultured in the absence of hydrogel for a period of time and in the presence of hydrogel for a period of time. When cultured in the presence of hydrogel, a cell can be mixed with the polymer network of the hydrogel in a liquid state (e.g., prior to gelation) and then gelation can occur after mixing (e.g., prior to culturing for a period of time). Culturing can occur in the liquid state and/or the gel state. In some cases, the hydrogel is in a gel state prior to mixing with cells and cells can penetrate the gel to incorporate and embed within the gel. In some cases, cells (e.g., ADMSCs, WAT-MSCs, pre-adipocytes, brown adipocytes, and/or a combination thereof) can be mixed with a subject composition in the liquid state and then implanted (e.g., injected) while the composition is still in the liquid state. In some cases, the composition will transition into a gel state after implanting (e.g., gelation can occur after injection). For example, in some cases, a cross-linker can be mixed (or co-injected) with the composition prior to implanting and the composition will transition into a gel state after implanting (e.g., gelation can occur after injection).

When a subject composition (e.g., a composition that includes cells) is to be implanted, the composition can have a combination of cell types (e.g., embedded within the hydrogel). For example, in some cases, 5% or more of the cells are brown adipocytes (10% or more, 15% or more, 20% or more, 25% or more, 30% or more, 35% or more, 40% or more, 45% or more, 50% or more, 60% or more, 70% or more, 80% or more, 90% or more, 95% or more, or 100%). In some cases, 5% or more of the cells are ADMSCs (10% or more, 15% or more, 20% or more, 25% or more, 30% or more, 35% or more, 40% or more, 45% or more, 50% or more, 60% or more, 70% or more, 80% or more, 90% or more, 95% or more, or 100%). In some cases, 5% or more of the cells are WAT-MSCs (10% or more, 15% or more, 20% or more, 25% or more, 30% or more, 35% or more, 40% or more, 45% or more, 50% or more, 60% or more, 70% or more, 80% or more, 90% or more, 95% or more, or 100%).

In some embodiments, cells (e.g., ADMSCs, pre-adipocytes, etc.) are cultured in (i.e., contacted with) basal differentiation medium (BDM). In some embodiments, ADMSCs are contacted with BDM for a period of time in a range of from 1 day to 7 days (e.g., 1 day to 7 days, 1 day to 6 days, 1 day to 5 days, 1 day to 4 days, 1 day to 3 days, 2 days to 7 days, 2 days to 6 day, 2 days to 5 days, 2 days to 4 days, 2 days to 3 days, 3 days to 7 days, 3 days to 6 days, 3 days to 5 days, 3 days to 4 days, 1 day, 2 days, 3 days, 4 days, 5 days, 6 days, or 7 days) (e.g., to induce differentiation), thereby generating a BDM-contacted cell population. In some embodiments, ADMSCs are contacted with BDM for 1 day or more (e.g., 2 days or more, 3 days or more, 4 days or more, 5 days or more, 6 days or more, or 7 days or more) (e.g., to induce differentiation), thereby generating a BDM-contacted cell population. In some cases, BDM-contacted cells are mixed with a subject hydrogel.

In some embodiments, cells (e.g., cells of a BDM-contacted cell population (e.g., either in the absence of hydrogel, or in the presence of hydrogel, e.g., after being mixed with hydrogel) are cultured in (i.e., contacted with) maintenance medium (MM) (can be in the presence or absence of hydrogel). In some cases, cells of a BDM-contacted cell population are contacted with MM for a period of time in a range of from 1 day to 14 days in maintenance medium (MM) (e.g., 2 days to 14 days, 3 days to 14 days, 4 days to 14 days, 5 days to 14 days, 6 days to 14 days, 7 days to 14 days, 8 days to 14 days, 9 days to 14 days, 10 days to 14 days, 10 days to 13 days, or 11 days to 13 days) to complete differentiation into UCP1 expressing adipocytes (i.e., brown adipocytes). In some cases, cells (e.g., cells of a BDM-contacted cell population) are contacted with MM for 1 day or more (e.g., 2 days or more, 3 days or more, 4 days or more, 5 days or more, 6 days or more, 7 days or more, 8 days or more, 9 days or more, 10 days or more, 11 days or more, 12 days or more, 13 days or more, or 14 days or more) to complete differentiation.

In some embodiments, the cells are autologous cells. As such, the cells and/or the progeny of the cells are derived from the same individual into whom the subject composition will be implanted. For example, autologous cells (e.g., ADMSCs, WAT-MSCs, etc.) can be obtained from an individual (e.g., via liposuction), incorporated into a subject composition, and then implanted into the individual. In some cases, the cells (e.g., autologous ADMSCs, autologous WAT-MSCs, etc.), are cultured in vitro for a period of time prior to implanting. Thus, in some cases, progeny of the isolated cells are implanted into the individual, and the progeny are still considered to be autologous.

Methods of increasing the number of brown adipocytes in an individual can provide for reduction of blood glucose to within a normal range (e.g, in individuals with diabetes), increased insulin sensitivity (e.g., in individuals with diabetes, e.g., type II diabetes), increased metabolic rate (e.g., in obese individuals and/or individuals with a reduced metabolism), weight loss (e.g., in individuals wishing to lose weight, obese individuals, and/or individuals with a reduced metabolism), and/or supplementation of endogenous heat production (e.g., in individuals prior to (or after) cold exposure, e.g., as a treatment for hypothermia; as a preventative measure for an individual who will spend time in a low temperature environment; as a preventative measure for an individual who will spend time in cold water; and the like).

In some embodiments, the number of cells (e.g., ADMSCs, WAT-MSCs, BDM-contacted cells, brown adipocytes, or a combination thereof) embedded within the hydrogel is in a range of from $1\times10^5$ cells to $1\times10^{10}$ cells (e.g., $1.5\times10^5$ cells to $1\times10^9$ cells, $1\times10^5$ cells to $1\times10^8$ cells, $1\times10^5$ cells to $1\times10^7$ cells, $1\times10^5$ cells to $1\times10^6$ cells, $1.5\times10^5$ cells to $1\times10^6$ cells, $2\times10^5$ cells to $5\times10^5$ cells, $4\times10^7$ cells to $1\times10^{10}$ cells, $1\times10^8$ cells to $1\times10^{10}$ cells, $1\times10^8$ cells to $5\times10^9$ cells, $3.5\times10^8$ cells to $5\times10^9$ cells, $4\times10^8$ cells to $2\times10^9$ cells, or $4\times10^8$ cells to $1\times10^9$ cells).

In some embodiments, the number of cells (e.g., ADMSCs, WAT-MSCs, BDM-contacted cells, brown adipocytes, or a combination thereof) embedded within the hydrogel is $1\times10^5$ or more cells (e.g., $1.5\times10^5$ or more, $2\times10^5$ or more, $2.5\times10^5$ or more, $3\times10^5$ or more, $3.5\times10^5$ or more, $4\times10^5$ or more, $4.5\times10^5$ or more, $5\times10^5$ or more, $5.5\times10^5$ or more, $6\times10^5$ or more, $5\times10^7$ or more, $1\times10^8$ or more, $1.5\times10^8$ or more, $2\times10^8$ or more, $2.5\times10^8$ or more, $3\times10^8$ or more, $3.5\times10^8$ or more, $4\times10^8$ or more, $4.5\times10^8$ or more, $5\times10^8$ or more, $5.5\times10^8$ or more, $6\times10^8$ or more, $7\times10^8$ or more, or $1\times10^9$ or more).

In some embodiments, the concentration of cells (e.g., ADMSCs, WAT-MSCs, BDM-contacted cells, brown adipocytes, or a combination thereof) embedded within the hydrogel is in a range of from $1\times10^5$ cells/ml to $1\times10^8$ cells/ml (e.g., $5\times10^5$ cells/ml to $5\times10^7$ cells/ml, $5\times10^5$ cells/ml to $1\times10^7$ cells/ml, $1\times10^6$ cells/ml to $1\times10^7$ cells/ml, $1\times10^6$ cells/ml to $7\times10^6$ cells/ml, or $2\times10^6$ cells/ml to $5\times10^6$ cells/ml).

In some embodiments, the concentration of cells (e.g., ADMSCs, WAT-MSCs, BDM-contacted cells, brown adipocytes, or a combination thereof) embedded within the hydrogel is $1\times10^5$ cells/ml or more (e.g., $1\times10^5$ cells/ml or more, $2\times10^5$ cells/ml or more, $3\times10^5$ cells/ml or more, $4\times10^5$ cells/ml or more, $5\times10^5$ cells/ml or more, $6\times10^5$ cells/ml or more, $7\times10^5$ cells/ml or more, $8\times10^5$ cells/ml or more, $9\times10^5$ cells/ml or more, $1\times10^6$ cells/ml or more, $2\times10^6$ cells/ml or more, $3\times10^6$ cells/ml or more, $4\times10^6$ cells/ml or more, $5\times10^6$ cells/ml or more, $6\times10^6$ cells/ml or more, $7\times10^6$ cells/ml or more, or $8\times10^6$ cells/ml or more).

In some cases, a cell-free composition is implanted into an individual and cells of the individual (e.g., naturally present ADMSCs, stems cells, mesenchymal stem cells (MSCs), etc.) are induced to differentiate (in vivo) into brown adipocytes.

In some cases, implanting a subject composition is performed in combination with administering to the individual at least one additional treatment regimen (e.g., a reduced calorie diet, administration of an agent that lowers blood glucose or increases insulin sensitivity, and the like) for treatment of a disorder.

In some cases, the additional treatment regimen includes administering to the individual a therapeutic agent (e.g., which is suitable in the treatment or prevention of one or more conditions selected from: type 1 diabetes mellitus, type 2 diabetes mellitus, impaired glucose tolerance (IGT), impaired fasting blood glucose (IFG), and a combination thereof). In some cases, administering a subject composition in combination with a therapeutic agent can reduce the dose of the therapeutic agent necessary to produce the desired results (e.g., in cases where the therapeutic agent is expensive, in cases where the therapeutic agent has side affects, and the like).

Examples of suitable therapeutic agents include, but are not limited to: biguanides, sulfonylureas, metiglinides, thiazolidindiones, alpha-glucosidase inhibitors, insulins and insulin analogues, dipeptidyl peptidase IV inhibitors (DPP IV inhibitors), SGLT 2 inhibitors, PPAR gamma/alpha modulators, glucose-dependent insulinotropic polypeptide agonists, beta-3 agonists, GLP1 and GLP1 analogues, PPAR gamma modulators, HMG-CoA reductase inhibitors, and PPAR delta modulators.

Examples of biguanides are metformin, phenformin, and buformin. A biguanide, Biguanides, for example metformin, can improve glycemic control, for example to reduce weight that has overall beneficial effects on the metabolic syndrome which is commonly associated with type 2 diabetes mellitus.

Examples of sulfonylureas are chlorpropamide, acetohexamide, tolazamide, glibenclamide, tolbutamide, glimepiride, glipizide, gliquidone, glibornurid, glyburide, and gliclazide. Administration of a sulfonylurea can result in better glycemic control.

Examples of meglitinides are nateglinide, repaglinide, and mitiglinide. Administration of a meglitinide can result in better glycemic control.

Examples of thiazolidindiones are pioglitazone, rosiglitazone, troglitazone, and ciglitazone. In combination with administration of a thiazolidinedione, for example rosiglitazone, implanting a subject composition can result in reduction in blood glucose, an improved glycemic control, an improvement of fluid retention caused by thiazolidindiones, and/or a reduction or nullification of weight gain associated with the use of thiazolidindiones.

Examples of alpha-glucosidase inhibitors are miglitol, acarbose, and voglibose. In combination with administration of an alpha-glucosidase inhibitor, implanting a subject composition can result in better blood glucose lowering, and/or a reduction in the necessary dose of an alpha-glucosidase inhibitor (which are commonly associated with unpleasant gastro-intestinal side effects), thereby making it more tolerable and improve the patients compliance with the treatment.

Examples of insulins and insulin analogues are short acting insulins like insulin lispro (Humalog®), insulin aspartat (Novorapid®), insulin glulisine (Apidra®, regular insulin, intermediate acting insulins like NPH-insulins and long acting insulins like lente, and ultralente insulin, insulin glargine (Lantus®), insulin detemir (Levemir®). The term "insulin" includes recombinant insulin. The use of insulin is commonly associated with weight gain as a result of the anabolic effects of insulin as well as fluid retention. Administration of insulin or an insulin analogue results in better glycemic control.

Examples of DPP IV inhibitors are denagliptin, carmegliptin, melogliptin, sitagliptin, vildagliptin, saxagliptin, linagliptin, dutogliptin, gemigliptin, and alogliptin. Administration of a DPP IV inhibitor can result in improved glycemic control.

Examples of SGLT 2 inhibitors are 6-(4-ethylbenzyl)-4-(β-D-glucopyranos-1-yl)-2-methoxy-benzonitrile; 2-(4-ethylbenzyl)-4-(β D-glucopyranos-1-yl)-5-methoxy-benzonitrile; 1-cyano-2-(4-ethylbenzyl)-4-(β-D-glucopyranos-1-yl)-5-methyl-benzene; 2-(4-ethylbenzyl)-4-(β-D-glucopyranos-1-yl)-5-hydroxy-benzonitrile; 2-(4-ethyl-benzyl)-4-(β-D-glucopyranos-1-yl)-benzonitrile; 2-(4-cyclopropyl-benzyl)-4-(β-D-glucopyranos-1-yl)-benzonitrile; 1-chloro-4-(β-D-glucopyranos-1-yl)-2-(4-ethynyl-benzyl)-benzene; 1-chloro-4-(β-D-glucopyranos-1-yl)-2-[4-((R)-tetrahydrofuran-3-yloxy-)-benzyl]-benzene; 1-chloro-4-(β-D-glucopyranos-1-yl)-2-[4-((S)-tetrahydrofuran-3-yloxy-)-benzyl]-benzene; 1-methyl-2-[4-((R)-tetrahydrofuran-3-yloxy)-benzyl]-4-(β-D-glucopyranos-1-yl)-benzene; 1-methyl-2-[4-((S)-tetrahydrofuran-3-yloxy)-benzyl]-4-(β-D-glucopyranos-1-yl)-benzene; dapagliflozin; atigliflozin; remogliflozin; sergliflozin; and canagliflozin. Administration of an SGLT 2 inhibitor can result in improved glycemic control.

Examples of PPAR gamma/alpha modulators are tesaglitazar, muraglitazar, and KRP297. Administration of a PPAR gamma/alpha modulator can result in improved glycemic control.

Examples of glucose-dependent insulinotropic polypeptide agonists are pramlintide, and amylin. Such therapeutic agents are expected to improve glycemic control.

Examples of beta-3 agonists are ritobegron, YM 178, solabegron, talibegronb, N-5984, GRC-1087, rafabegron, and FMP825. Administration of a beta-3 agonist can result in improved glycemic control.

Examples of GLP1 and GLP1 analogues include exenatide, liraglutide, and taspoglutide. Administration of a GLP1 and/or GLP1 analogue can result in improved glycemic control and result in weight reduction.

An example of a PPAR gamma modulator is metaglidasen. Administration of a PPAR gamma modulator can result in improved glycemic control.

Examples of HMG-CoA reductase inhibitors are simvastatin, lovastatin, and provastatin. Administration of an HMG-CoA reductase inhibitor can result in improved glycemic control.

Examples of PPAR delta modulators are GW 501516, GW 0742, L165041, LY 465608, and L-796449.

Implanting a Subject Composition

In another aspect, provided herein is a method of introducing a subject composition (having at least a hydrogel and a cell adhesion ligand) into a mammalian subject. Because the subject hydrogels have a reasonable working time (e.g., 5-10 minutes) prior to gelation the material (e.g., in liquid form) can be injected through an 18-28-gauge needle, which facilitates implantation. A subject hydrogel, prior to gelation, can be injected into a mammalian subject in any convenient location, depending on the desired outcome. As a non-limiting example, an acellular or cell-containing formulation of a subject hydrogel cell can be implanted (e.g., injected) subcutaneously.

As another non-limiting example, in order to treat diabetes or obesity, a subject hydrogel can comprise an enhancement compound (or combination of enhancement compounds)(e.g., as described above) that promotes differentiation into, and/or maintenance of brown adipocytes, and the hydrogel. In some cases, a subject composition can be injected into existing fat pads. As another non-limiting example, in order to treat diabetes or obesity, and/or to supplement endogenous heat production, a subject hydrogel can comprise a brown adipocyte, a brown adipose stem cell, a brown adipose progenitor cell, an ADMSC, and/or a WAT-MSC, and the hydrogel can be injected into the individual (e.g., an existing fat pad, between the shoulder blades, etc.).

Mammalian subjects (i.e., individuals) include, but are not limited to, rodents (e.g., rats; mice); canines; ungulates (bovines; caprines; ovines; etc.); felines; lagomorphs (e.g., rabbits); non-human primates; and humans. In some embodiments, the individual is a human.

In some cases, a method of increasing the number of brown adipocytes in an individual includes inducing the differentiation of a cell (e.g., a population of cells) (e.g., an ADMSC or population of ADMSCs) into a brown adipocyte (e.g., a population of brown adipocytes) (e.g., as described above) and implanting a subject composition (e.g., comprising brown adipocytes) into an individual.

Implanting (e.g., injection) can be performed at any convenient location in the body. Suitable locations include, but are not limited to: a highly vascular location (e.g., a location that is close to blood supply) (e.g., neck, intrascapular, and the like); an inconspicuous location (e.g., if the implantation is for weight loss) (e.g., thighs, buttocks, and the like); a location near neurons; etc.

Implanted compositions can be removed. In some embodiments, the subject methods include removing an implanted composition. In some cases, removing an implanted composition can be accomplished surgically (e.g., surgically removing an implanted hydrogel).

Evaluation of BAT-MACTs

A subject composition having brown adipocytes that can be implanted into an individual can be referred to as a brown adipose tissue matrix assisted cell transplant (BAT-MACT). In some embodiments, a subject method can include a step of evaluating the success of a transplant. Any convenient method of evaluation may be used. Exemplary methods of evaluation include, but are not limited to:

(a) BAT-MACT persistence and atrophic effects on endogenous BAT. For example, using luciferase based in vivo imaging, as shown in the Examples. For example, BAT-MACTs can be isolated after implantation at any convenient time point (e.g., 1 day to 7 days after implantation, 7 days to 10 days after implantation, 10-14 days after implantation, 7-14 days after implantation, 7-21 days after implantation, 1 day or more after implantation, 2 days or more after implantation, 3 days or more after implantation, 7 days or more after implantation, 10 days or more after implantation, 14 days or more after implantation, 21 days or more after implantation, etc.) to determine changes in tissue architecture, vascularization, innervation, gene expression patterns, and the like. Long-term effects on the total mass and tissue morphology of the endogenous BAT in implant recipients can also be tested for potential compensatory atrophy.

(b) Determine maintenance of BAT phenotype (e.g., using any of the described brown adipocytes assays, e.g., measuring the expression level of a brown adipocyte biomarker, assaying for lipid droplets, etc.) (see, e.g., Example 1).

(c) Assess vascularization. Vascularization of implants can aid their survival and function. Vascularization can be assessed by any convenient method (e.g., visual assessment, staining of implant sections with endothelial markers (e.g., CD31, endomucine, etc.), and the like) (see, e.g., Example 1). Microvascular density can be scored using automated and manual analysis of tissue sections. In addition, functional tests can be performed (e.g., by injecting animals prior to implant removal with India Ink followed by microscopic imaging, which will assess whether blood vessels throughout the BAT-MACT (i.e., implanted composition) are and/or were functionally connected to the host's circulation).

(d) Innervation. Recruitment of sympathetic neurons that can locally release (nor)epinephrine, which can affect cold activation of BAT-MACTs, and could also play a role in maintaining cell differentiation. Catecholamine producing cells can be identified in tissue sections using tyrosine hydroxylase staining. Strategies to further stimulate norepinephrine releasing cells can be used.

(e) Imaging of glucose and fatty acid uptake. The ability of BAT-MACTs to consume calories in the form of glucose and fatty acids can be assayed. To this end, glucose and fatty acid uptake of implants can be assayed (e.g., using positron emission tomography (PET) and bioluminescent imaging). (i) PET imaging: PET imaging of glucose and fatty acid uptake can be performed before and after injection of a β-adrenergic agonist (e.g., CL316243) using 18F-2-deoxyglucose and 11C-palmitate. (ii) Bioluminescent imaging of fatty acid. a bioluminescent assay for the assessment of fatty acid uptake in vivo can be used. For example, when using luciferase expressing cells, the light signal will only be generated by the transplanted but not host cells. Fatty acid uptake can be monitored before and after injection of a β-adrenergic agonist (e.g., CL316243) (see, e.g., Example 1).

(f) Monitoring weight gain (see, e.g., Example 1).

(g) Direct and indirect calorimetry. To determine the impact of BAT-MACTs on basal and stimulated metabolic rates, direct and indirect calorimetry can be used. (i) Direct calorimetry: Core body temperature can be recorded either at room temperature or when exposed to a different temperature (e.g., cold such as 4° C.) (see, e.g., Example 1). (ii) Indirect calorimetry: A CLAMS metabolic chamber system can be used to record basal and a β-adrenergic agonist (e.g., CL316243) stimulated respiration rates and heat production (as well as movement) (e.g., in the present and/or absence of food) (see, e.g., Example 1).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

A cell scaffold technology optimized to differentiate and support the implantation of UCP1 expressing adipocytes is presented. To this end, the biophysical properties of hyaluronic acid-based hydrogels were adapted to support the differentiation of white fat derived multipotent stem cells (ADMSCs) into lipid accumulating, UCP1 expressing, brown fat-like cells. Subcutaneous implantation of ADMSCs within optimized bioinspired hydrogels resulted in the establishment of distinct UCP1 expressing implants that successfully attracted host vasculature and persisted for several weeks. Importantly, implant recipients demonstrated elevated core body temperature during cold challenges, enhanced respiration rates, improved glucose homeostasis, and reduced weight gain, demonstrating the therapeutic effect of this highly translatable approach.

Methods

Synthesis of HyA Hydrogels

HyA derivative modified HyA (500 kDa) with a hydrazide group (HyAADH) was synthesized using previously established methods[64]. Acryloxysuccinimide (700 mg) was subsequently reacted with the HyAADH solution (300 mg, 100 mL deionized (DI) water) to generate acrylate groups on the HyA (AcHyA). AcHyA was evaluated by 1H NMR. The AcHyA-C16 or AcHyA-Ag73 was synthesized by reacting peptide (CGGKAFDITYVRLKF (SEQ ID NO:9), 10 mg) or (CGGRKRLQVQLSIRT (SEQ ID NO:8), 10 mg) with AcHyA (25 mg, 10 ml deonized (DI) water) at room temperature. To synthesize the HyA hydrogel, AcHyA, AcHyA-C16 (6 mg), and AcHyA-Ag73 (2 mg) were dissolved in 0.3 mL of triethanolamine-buffer (TEOA; 0.3 M, pH 8), and incubated for 30 minutes at 37° C., subsequently an MMP-13-cleavable crosslinker (CQPQGLAKC (SEQ ID NO:39), 3 mg 50 µL TEOA buffer) was added to HyA-peptide solution, which will react with free acrylate groups found on the HyA macromer chains. The crosslinker concentration was varied to achieve complete crosslinking of available acrylate functionalities on the HyA macromers, roughly 200 µM. The initial storage modulus of all hydrogels (in vitro and in vivo) were measured to be consistently ~850 Pa.

Rheology

Viscoelastic properties of the hydrogel were determined using an oscillatory rheometer with parallel plates geometry (8 mm) and a gap height of 0.2 mm under 10% constant strain and frequency ranging from 0.1 Hz to 10 Hz at 37° C. in a humidity-controlled chamber.

ADMSC Isolation

Fat depots from L2G85 (FVB/NJ) or C57BL6/J mice, perigonadal (visceral) or inguinal (subcutaneous) respectively, were isolated post mortem from 3 month old mice.

These fat depots were washed with sterile phosphate buffered saline (PBS) for 10 minutes. The tissues were then minced with scissors into fragments smaller than 1 mm and digested in 0.1% type II collagenase (Gibco) in DMEM with 5% bovine serum albumin (BSA) (Fisher) for 1 hr at room temperature (RT) on an orbital shaker. The digest was then filtered through sterile gauze and centrifuged at 400×RCF for 10 minutes. The cell pellet was then suspended in an erythrocyte lysis buffer 155 mM $NH_4Cl$, 5.7 mM $K_2HPO_4$, 0.1 mM EDTA in ultrapure water for 10 m minutes. The resulting suspension was then centrifuged at 400×RCF for 10 minutes to pellet the ADMSCs. The resulting ADMSC pellet was suspended in DMEM with 10% fetal bovine serum (FBS) and 1% P/S and plated on TCPS.

BAT-MACT Generation

ADMSCs were cultured in vitro in DMEM with 10% FBS and 1% Penicillin/Streptomycin (P/S) on TCPS. 2 days post confluence, differentiation was induced with 0.85 µM Insulin, 10 nM Triiodothyronine, 1 µM Dexamethasone, and 500 µM Isobutylmethylxanthine (for WAT-MACT, triiodothyronine was omitted from the cocktail). 3 million cells per mL were suspended in AcHyA-Ag73:C16 [1:3 molar ratio] just before implantation (for WAT-MACT cells were suspended in AcHyA). The cell suspension was mixed with the MMP13 cleavable crosslinker and then 100 µL of the forming BAT-MACT was immediately injected to recipient mice.

Cell Adhesion Assays

Purified peptides were suspended at 20 µM in ultrapure water with 1% P/S. In 24 well TC plates (BD Falcon, 353047), 20 µM peptide suspensions were added to each well. Peptides adsorbed to the TCPS overnight at 4° C. Plates were then washed 2 times with PBS. 20,000 primary ADMSCs suspended in DMEM with 10% FBS and 1% (P/S) were added to each well and incubated at 37° C. for 4 hours. Media and non-adherent cells were removed and centrifuged to separate the cells from media. The adherent and non adherent cells were then counted with the CyQuant kit (Invitrogen).

Reverse Transcription/Polymerase Chain Reaction (rtPCR)

Tissue samples suspended in RNALater ICE (Ambion) and stored at −20° C. mRNA was isolated from RNALater ICE stabilized tissues or directly from in vitro cultures of monolayers or cell laden hydrogels with Trizol reagent (Ambion). Tissue suspensions were homogenized with a Polytron PT2100. Assays were carried out on an ABI 7500 RT PCR System with TaqMan universal mastermix II and validated PrimeTime primer probe sets (IDT). First strand cDNA synthesis kit (Fisher) was employed to transcribe 5 µg of RNA per 20 µL 100 ng of cDNA was used per rtPCR reaction in triplicates. Established delta delta CT method was employed to comparatively assess mRNA quantity. All data is represented as sample's value normalized to GAPDH relative to source tissue or endogenous BAT.

Protein Quantification and Western Blotting

Protein was isolated from the remaining portion of the Trizol suspension after mRNA extraction according to the Ambion Trizol™ Reagent protocol. 10 µg of protein was loaded into Novex 4-20% tris glycine precast gels (Life). Transferred with the iBlot (Invitrogen) system. Assayed with anti UCP1 (Invitrogen) and anti β-tubulin E7 clone (DSHB). Li-Cor Oddessy was employed to image and quantify bands.

Animals and Diets

Experiments were done according to AAALAC guidelines. Procedures were approved by the University of California-Berkeley Animal Care and Use Committee. 8 week old male C57BL/6J (Laboratories (catalog #000664) or FVB/NJ Mice (catalog #001800) were purchased from Jackson Labs. Mice were group housed for a one-week acclimation period (temperature: 70±4° F., humidity: 30-70%). Then the mice were housed in individual cages in an environmentally controlled room and given an additional weeklong acclimation period before the implantation of BAT-MACT condition and the high 60% fat diet (Teklad TD.06414). Luciferase expressing L2G85 (FVB/NJ) mice were utilized as cell source for experiments using bioluminescent monitoring of implant viability.

Serum Glucose and Glucose Tolerance Tests

Blood glucose was measured at noon with a NovaMax™ blood glucose monitor and NovaMax™ glucose test strips (Sanvita). Tails were minimally punctured with a sterile razor blade, only deep enough to produce a few µL of blood when the tail was massaged around the puncture. The initial droplet of blood produced was discarded; the subsequent droplet was used to measure blood glucose. Body weight was measured at this same time with an Ohaus Navigator Scale (NV212).

For glucose tolerance tests (GTTs), mice were injected with an equal dose of glucose (167 µL of 300 g/L glucose). This dose was selected as a dose that the median mouse weight would warrant to achieve the standard glucose does of 2 mg/g body weight generally used for a GTT. Glucose measures were taken as previously described at 0, 20, 30, 60, and 120 min after glucose injection.

Cold Challenge and Core Body Temperature

Physitemp Model BAT-12 microprobe was employed to measure core body temperature of mice rectally. Cold challenges took place in a 4° C. walk in refrigerator approved for use by AAALAC guidelines. Mice were individually housed and fed ad lib in Tecniplast cages filled with sani-chip bedding (Harlan).

Immunohistochemistry

Tissues were fixed with 4% paraformaldahyde for 1 hr at 4° C., and were incubated overnight at 4° C. with of 30% sucrose in blocking media (1×HBSS with 5% FBS, 0.1% BSA, 0.05% Saponin, and 0.1% Tween20). Tissues were sectioned with a depth of either 12 µM, 20 µM, or 50 µM. Sections were washed multiple times and then blocked with blocking media for 1 hour. Subsequently, sections were incubated with their corresponding primary antibody for 1.5 hours at RT. Sections were then washed with fresh blocking media for 20 min, and then with PBST with 0.05% Saponin 2 times for 10 minutes. Secondary antibodies were diluted into the blocking media and applied to sections for 1 hr at room temperature. Then sections were washed with the same procedure that followed the primary antibody treatment. Subsequently, coverslips were mounted with DAPI/glycerol mounting medium (Life Technologies cat#S36938). Slides were stored at −20° C. until imaging with a Zeiss LSM710 Confocal microscope.

Whole in vitro hydrogels were fixed with 4% PFA for 30 minutes at RT and imaged in their MilliCell (PICM01250) placed on a coverslip.

Bioluminescent Imaging

Imaging was accomplished with an IVIS Spectrum. 45 µL luciferin (BioVision #7902) [4 mg/mL] in PBS was injected into animals intraperitoneally (IP). FFA-SS-LUC 100 µl of [1.4 µg/µl] compound injected IP into mice. Once the BLI signal dropped off (40 minutes) the animals were removed to recover. 4 hr later once all original BLI signal was extinguished, 1 µg CL316,243 per gram body weight was injected IP followed by another dose of the FFA-SS-LUC.

Respirometry

CLAMS, Comprehensive Laboratory Animal Monitoring System, Columbus Instruments, Columbus Ohio, US. Measurements were taken over a 24 hour period and average values were assessed. CL-316,243 was administered to animals and the 4 hour prior were compared to the 4 hours post injection.

Activity was monitored in 8 min intervals as infrared beam breaks in X, Y and Z-axis and found to be not significantly different for any of the groups.

Thermography

IR thermography was accomplished with a FLIR T650 thermal imaging camera.

Statistical Analysis

All data is presented as SEM analyzed using Prism (graphpad). Statistical significance was determined by one-way ANOVA followed by Tukey post test or unpaired two-tailed student's t-test. Significance presented at *(P<0.05), **(P<0.01), and (P<0.001).

Results

Optimization of Adhesion Ligands for UCP1-positive Adipocyte Differentiation

The importance of cell adhesions and matrix interactions has well-documented effects on MSC differentiation; however, no screens to enhance BAT-like differentiation of white adipose tissue derived MSCs (ADMSCs) have been reported thus far. To this end, ADMSCs were derived from mouse white fat pads (inguinal and epididymal) using an effective isolation technique[25], and were cultured on tissue culture polystyrene (TCPS) plates coated with highly specific peptides found to be ligands for various integrins and syndecans (FIG. 1A) (Table 4).

TABLE 4

| Acronym | Peptide Sequence | Receptor Target | Protein Source |
|---|---|---|---|
| bsp-RGD | CGGNGEPRGDTYRAY (SEQ ID NO: 42) | $\alpha_v\beta_3$ | Bone sialo-protein, vitronectin |
| P3 | CGGVSWFSRHRYSPFAVS (SEQ ID NO: 43) | $\alpha_6\beta_1$ | Laminin α1 chain |
| AG10 | CGGNRWHSIYITRFG (SEQ ID NO: 44) | $\alpha_6\beta_1$ | Laminin α1 chain |
| AG32 | CGGTWYKIAFQRNRK (SEQ ID NO: 45) | $\alpha_6\beta_1$ | Laminin α1 chain |
| AG73 | CGGRKRLQVQLSIRT (SEQ ID NO: 8) | Syndecan-1 | Laminin α1 chain |
| C16 | CGGKAFDITYVRLKF (SEQ ID NO: 9) | $\alpha_v\beta_3$, $\alpha_5\beta_1$ | Laminin γ1 chain |

Table 4: Adhesion peptides. Peptide targets for integrins and other adhesion receptors present on stem and progenitor cells identified via RT-PCR, immunofluorescence, confocal microscopy, or flow cytometry. Peptides listed in Table 4 include an N-terminal "CGG" sequence; for example, AG73 has the sequence: RKRLQVQLSIRT (SEQ ID NO:1), and in Table 4 includes an N-terminal "CGG" sequence.

Figure 1C:
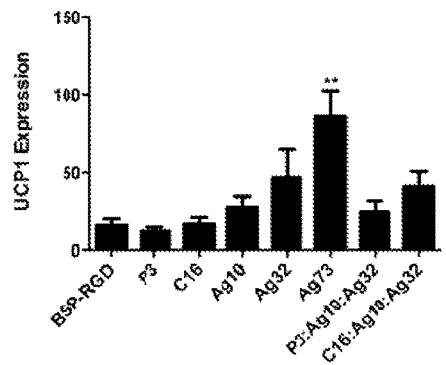
Figure 1D:
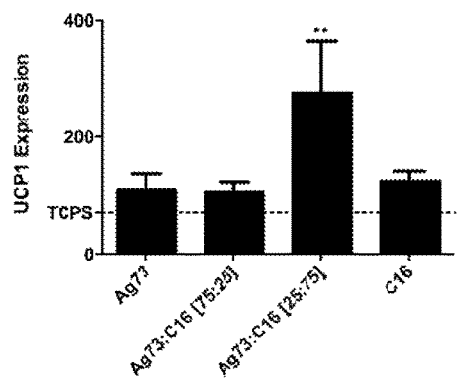
Figure 1E:
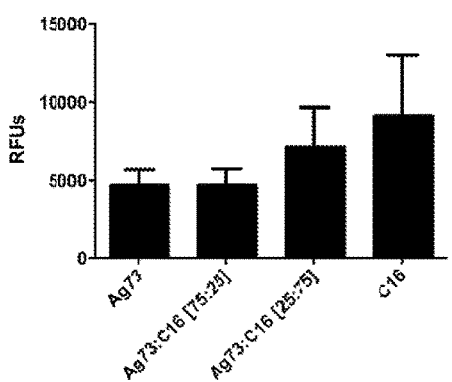
Figure 1F:
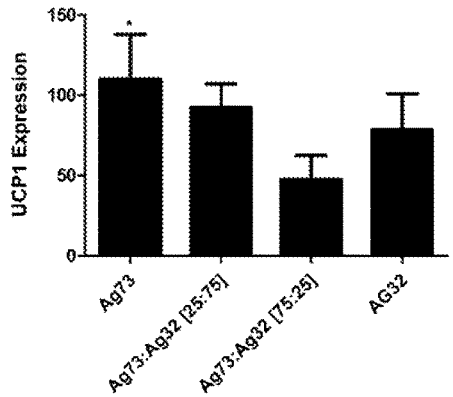

Differentiation was induced (see Methods section), and lipid droplet accumulation (FIG. 1B) as well as UCP1 expression were assessed (FIG. 1c). Initial screens identified non-RGD peptide sequences such as AG73 (CG-GRKRLQVQLSIRT; SEQ ID NO:8), an adhesion ligand for $\alpha_6$ integrins and syndecan-1[26-28], as particularly efficient in driving UCP1 expression of BAT differentiated ADMSCs, while C16 (CGGKAFDITYVRLKF; SEQ ID NO:9), an $\alpha_5\beta_{1/3}$ integrin-engaging ligand[29], supported significantly greater lipid accumulation, which likely reflects an activation of lipid uptake and metabolism related genes. Interestingly, while all peptide-coated substrates outperformed uncoated TCPS in UCP1 expression assays, a combination of AG73 with C16 (1:3 molar ratio) had significant synergistic effects on UCP1 expression (FIG. 1D), but not lipid accumulation (FIG. 1E). Combining varied concentrations of AG73 with AG32 (CGGTWYKIAFQRNRK; SEQ ID NO:45), a specific $\alpha_6\beta_1$ integrin-engaging ligand[28], had limited and diminishing effects on UCP1 expression (FIG. 1.F). The impressive gain in differentiation and UCP1 expression achieved by optimizing adhesion ligands is highlighted by the fact that previous attempts to differentiate WAT-derived MSCs into BAT yielded UCP1 levels equivalent to ~1% of those found in differentiated BAT-derived MSCs[14]. In contrast, it was shown that UCP1 expression by WAT-derived ADMSCs differentiated on optimized adhesion ligands actually achieves comparable UCP1 expression to differentiated BAT-derived ADMSCs in vitro.

FIGS. 1A-F: Effects of adhesion ligands ADMSC differentiation. A) Adhesion of ADMSCs to adsorbed peptides (see Tab. 1) to the surface of tissue culture (TCPS) after 4 hr, relative fluorescent units of adherent cells (n=3). B) Neutral lipid staining of ADMSCs after differentiation on indicated adhesion substrate coated TCPS (n=3). C) Quantitative rtPCR analysis of UCP1 expression of WAT derived murine ADMSCs that were differentiated on indicated adhesion substrate coated TCPS (see Tab. 1) (n=3). D) Quantitative rtPCR analysis of UCP1 expression of WAT derived ADMSCs differentiated on mixtures of Ag73 and C16 (n=6). E) Neutral lipid staining of WAT derived ADMSCs on varied mixtures of Ag73 and C16 (n=6). F) Quantitative rtPCR analysis of UCP1 expression of WAT derived ADMSCs differentiated on mixtures of Ag73 and Ag32 (n=6).

Figure 2A:
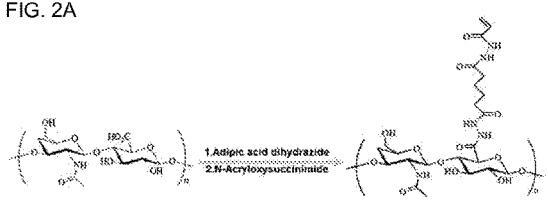
FIGS. 2A-G depict features of exemplary hyaluronic acid based hydrogels (HyA hydrogels).
Figure 2B:
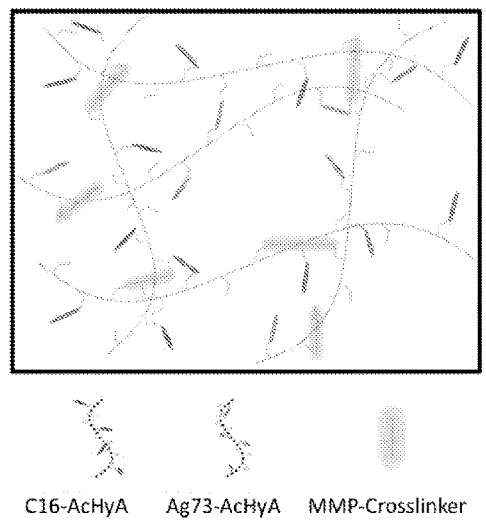
Figure 2C:
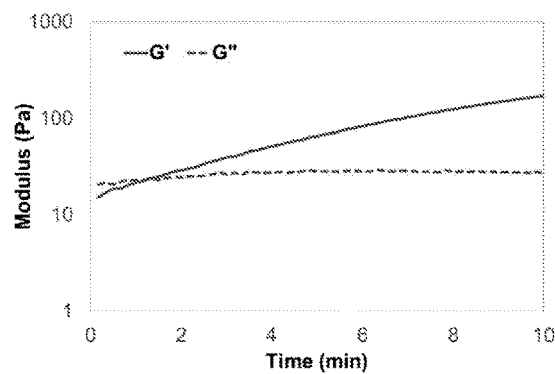
Figure 2D:

Engineering Optimized Hydrogel Scaffolds for Support and Development of UCP1 Positive Cells Engagement of cells with extracellular matrix provides a crucial factor in driving MSC differentiation based on matrix biophysical properties and composition[30-33]. Acrylated HyA (AcHyA) macromers were synthesized (FIG. 2A), which were further functionalized through conjugation of the differentiation mediating peptides to the AcHyA. These functionalized AcHyA macromers (AcHyA-Ag73, and AcHyA-C16) were combined with specific matrix metalloprotease (MMP) sensitive peptide crosslinkers at defined concentrations to form hydrogels with precise physical characteristics as well as biologically facilitated degradation kinetics (FIG. 2B). The synthesis of hydrogel network takes advantage of the Michael-type addition reaction (i.e., attack of the acrylate group by available cysteine thiols to form a covalent bond)[40,41], and forms defined hydrogel scaffold within 5 minutes (FIG. 2C, FIG. 2D).

Figure 2E:
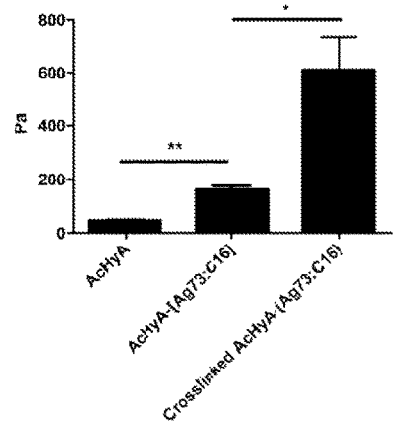
Figure 2F:
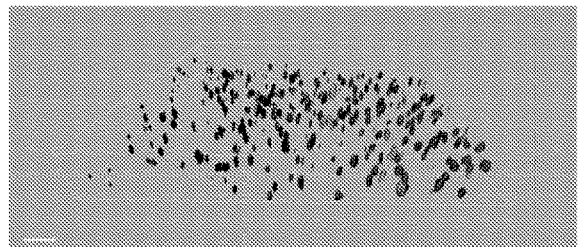
Figure 2G:
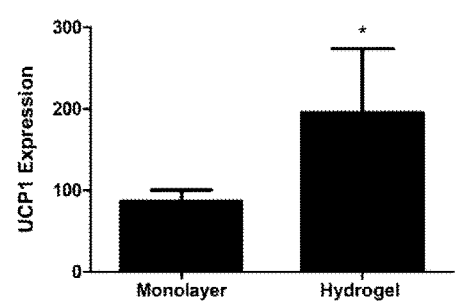

ADMSCs embedded in the optimized matrix were forming functional cell adhesion sites with the biologically inspired hydrogel instead of being passively trapped in a crosslinked matrix; this was verified by suspending ADMSCs in uncrosslinked AcHyA-Ag73:C16 or unmodified AcHyA. It was found that the inclusion of adhesion peptides resulted in a significant increase in storage modulus, indicating the inclusion of these adhesion peptides mechanically integrated the cells with the synthetic ECM (FIG. 2E). The optimized hydrogel scaffold allowed the ADMSCs to evenly distribute and differentiate into UCP1 positive adipocytes in vitro without direct cell-cell contact (FIG. 2F). Importantly, culturing cells in AcHyA-Ag73:C16 hydrogels significantly improved UCP1 expression of differentiated ADMSCs in vitro (FIG. 2G) compared to cell monolayers exposed to adsorbed Ag73:C16.

FIGS. 2A-G: Bio-inspired HyA hydrogels. A) Schematic of the synthesis of acrylated hyaluronic acid (AcHyA) by sequential conjugation of adipic acid dihydrazide and N-acryloxysuccinimide. B) Representation of the assembly of optimized hydrogel through crosslinking of C16-AcHyA to Ag73-AcHyA macromers with an MMP degradable crosslinker (not to scale). C) Timeline of HyA hydrogel gelation, gelation was considered complete when the storage modulus (G') exceeded the loss modulus (G'') (measured in Pascals). D) Photographs of AcHyA before (left) and 5 min after the addition of the crosslinker (Right). E) Storage modulus of ADMSC seeded uncrosslinked and crosslinked hydrogels cultured in vitro after 72 hr (n=3). F) 3D reconstruction of in vitro ADMSCs in optimized hydrogel (UCP1 in red, mitotracker in green) after completion of differentiation. G) UCP1 expression of differentiated ADMSCs with the optimized peptide mixture in monolayer and comparable hydrogel (n=4).

Matrix Assisted Cell Transplantation of Brown Adipose-like Tissue

Figure 3A:
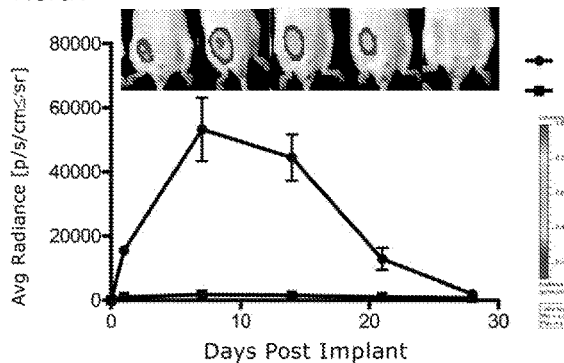
FIGS. 3A-G depict brown adipose tissue matrix assisted cell transplant (BAT-MACT) in vivo.
Figure 3B:
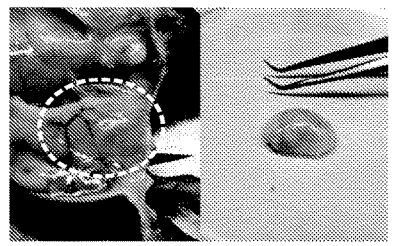
Figure 3C:
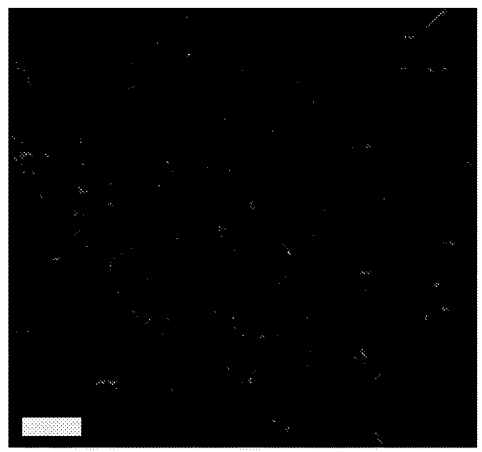
Figure 3D:
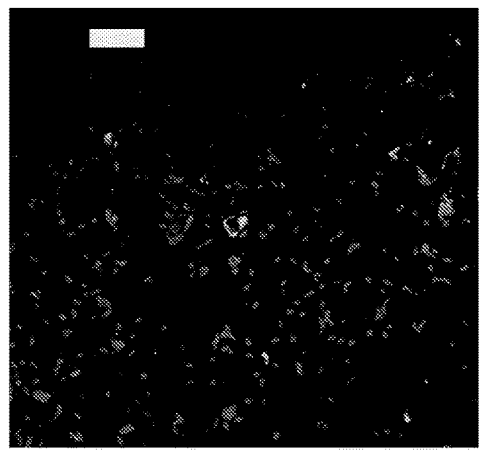
Figure 3E:
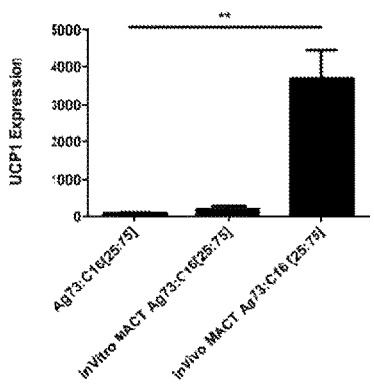
Figure 3F:
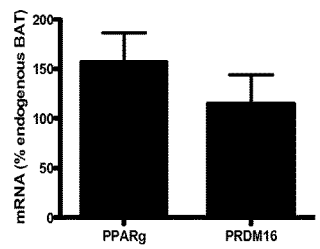

To produce a functional BAT-MACT in mice ADMSCs were isolated from donor WAT, initiated differentiation in vitro; and the cells were then suspended in Ag73 and C16 presenting AcHyA macromers. BAT-MACTs were loaded with ~3 million cells per mL AcHyA macromers (3 wt %), unless otherwise specified. The MMP sensitive crosslinker was added to the cell suspension, which was immediately injected with a 22.5 gauge needle into the subcutaneous inguinal fat pad of recipient animals. The viability of the implanted BAT-MACT was monitored via bioluminescence of luciferase expressing donor cells using cell free matrices as control for background signal. Using this approach, signal expansion was observed during the first week, followed by a decline in cell number reaching undetectable levels after 4 weeks (FIG. 3A). Due to the rapid crosslinking kinetics, the BAT-MACT forms a distinct subcutaneous lobe upon injection that is clearly brown/beige in appearance (FIG. 3B). BAT-MACTs were highly vascularized by the surrounding blood vessels on a macroscopic level and thin sections of implants demonstrated extensive and even distribution of a vascular network throughout the implants (FIG. 3C). Likewise, UCP1 positive and lipid droplet accumulating cells were evenly spread throughout the BAT-MACT (FIG. 3D). Interestingly, regions of the implant showed positive staining for tyrosine hydroxylase, the rate-limiting enzyme in the synthesis of catecholamines. Tyrosine hydroxylase is essential for the production of norepinephrine either by sympathetic neurons or by BAT resident macrophages and has been suggested to not only activate respiration, but also to maintain differentiation status and function[42-47]. UCP1 mRNA expression of the implanted MACT was over 10 fold higher than that of comparable in vitro cultured MACTs (FIG. 3E) and reached 12-17% of the level found in endogenous BAT. Importantly, PRDM16 and PPARgamma expression levels in BAT-MACTs were as high as in endogenous BAT (FIG. 3), indicating the high BAT-like differentiation potential of the matrix embedded cells.

Figure 3G:
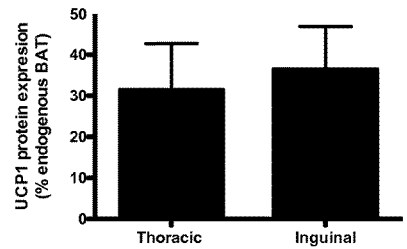

To assess the effect of implant location, two different implant sites in the thoracic and inguinal regions were analyzed for lipid droplets and UCP1 expression. In BAT-MACTs from both implantation sites numerous small lipid droplets as well as numerous UCP1 positive cells and blood vessels were observed, with no apparent difference between the implantation sites. UCP1 protein levels from thoracic and inguinal implants were determined by SDS-PAGE using endogenous classical BAT as a control and tubulin to normalize for protein levels. Impressively, UCP1 protein levels in both BAT-MACT sites reached around 30% of that found in classical BAT from the same animals (FIG. 3G).

FIGS. 3A-G: BAT-MACT in vivo. A) Persistence of BAT-MACT over time monitored by luciferase activity in live animals (n=5). False color heat-scale image indicting average photon radiance. B) Macroscopic morphology of implants after 2 weeks. BAT-MACTs were removed after 14 days fixed, cryosectioned, and stained with DAPI and C) vascularization marker endomucin (red), D) neutral lipids (green) and UCP1 (red). E) Quantitative rtPCR analysis of UCP1 expression of differentiated ADMSCs plated on optimized molar ratio of Ag73 and C16, in a hydrogel composed of Ag73 and C16 conjugated AcHyA macromers cultured in vitro or implanted into recipient animals normalized to GAPDH relative to WAT (n=4, 3, or 6 respectively). F) PRDM16 and PPARgamma gene expression of BAT-MACTs after 2 weeks in vivo normalized to GAPDH, relative to endogenous BAT (n=9). G) Relative UCP1 protein in BAT-MACTs of different implant sites after 2 weeks in vivo normalized to β-tubulin relative to endogenous BAT (n=5).

Metabolic Impact of BAT-MACTs

Figure 4A:
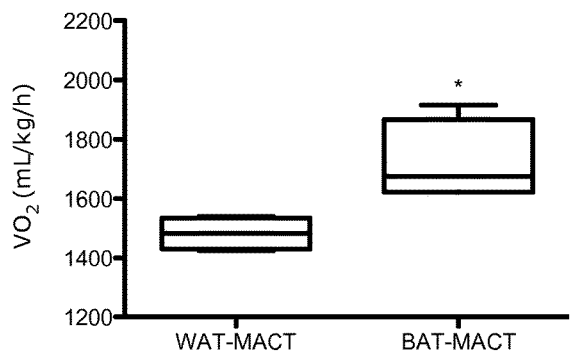
FIGS. 4A-F depict metabolic effects of BAT-MACTs.
Figure 4B:
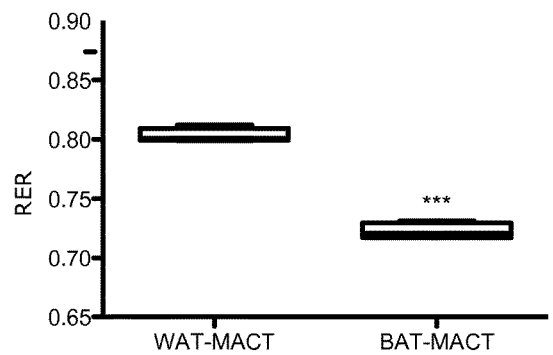
Figure 4C:
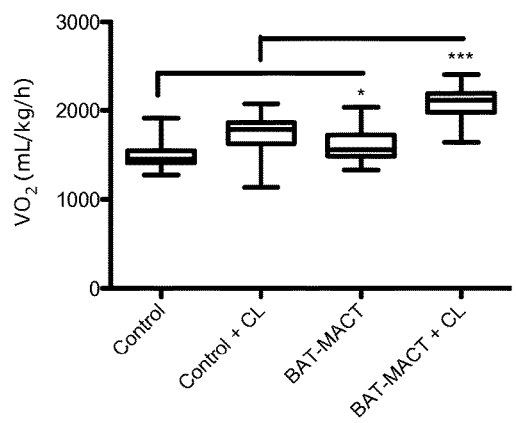
Figure 4D:
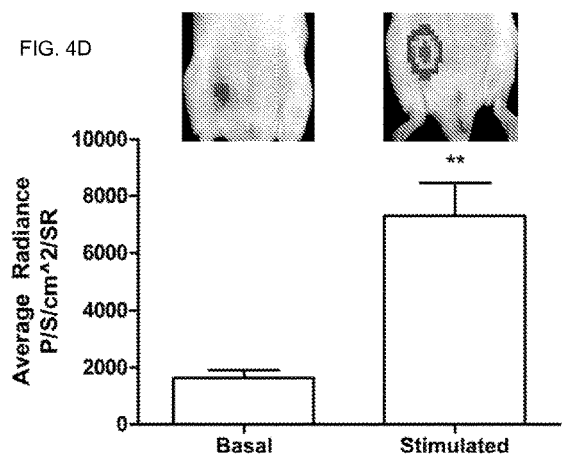

To determine the metabolic impact of BAT-MACTs, the respiratory capacity of animals that received the optimized matrix BAT-MACT or an implant of an identical density of white adipocytes scaffolded by hyaluronic acid (WAT-MACT), which has been shown to aid in the development and persistence of WAT[48, 49-51], was examined. The BAT-MACT implanted animals displayed significantly enhanced oxygen consumption rate ($VO_2$) and reduced respiratory exchange ratio (RER), recapitulating the elevated fatty acid utilization and respiration following classical BAT activation (FIG. 4A, FIG. 4B). Furthermore, BAT-MACT augmented animals were significantly more responsive to CL-316,243, a β3-specific adrenergic agonist (FIG. 4C). To verify that that albumin bound fatty acids from the circulation can indeed be delivered to and taken up by BAT-MACTs, a recently developed optical probe for fatty acid uptake[52] was utilized. It was observed that an intraperitoneal injection of the probe was robustly taken up by BAT-MACTs. Importantly, as previously shown for endogenous BAT[53], injection of a β3 adrenergic agonist significantly enhanced fatty acid uptake rates by the BAT-MACTs (FIG. 4D).

Figure 4E:
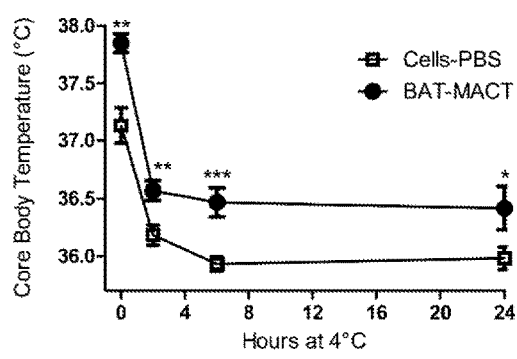
Figure 4F:
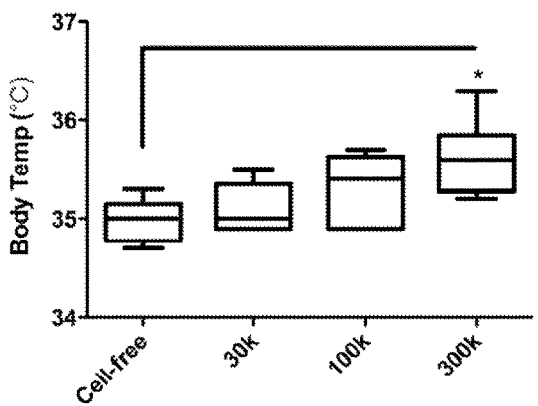

To test the impact of BAT-MACTs on thermogenesis core body temperature at room temperature (21° C.), and during a 24 h 4° C. cold exposure, was determined. Body temperatures of BAT-MACT recipients were significantly higher at all time points during cold exposure as well as at room temperature (FIG. 4E). Thermography revealed that the implant is distinctly thermogenic, even at 21° C. Importantly, this thermogenic effect was proportional to the amount of cells implanted (FIG. 4F).

FIGS. 4A-F: Metabolic effects of the BAT-MACT. A) Average oxygen consumption ($VO_2$) rate over 24 hours (n=4). B) Average respiratory exchange ratio over 24 hours (n=4). C) Average oxygen consumption rate 4 hr before and after β-adrenergic agonist cl-316,243 was administered (n=4). D) Fatty acid uptake of BAT-MACTs under basal and -adrenergic agonist cl-316,243 stimulated conditions (FFA-SS-Luc) (n=3). E) Core body temperature during 24 hour cold challenge (4° C.) (n=6). F) Core body temperature of animals receiving varied ADMSC concentrations in 100 µL of optimized hydrogels after 6 hr cold challenge (4° C.) (n=6). Explanation of WAT-MACT: ADMSCs differentiated without T3 embedded in a hyaluronic acid hydrogel containing not optimized peptide conjugations. Explanation of Cells-PBS: equivalent number of differentiated ADMSCs delivered in 100 µL PBS.

Figure 5A:
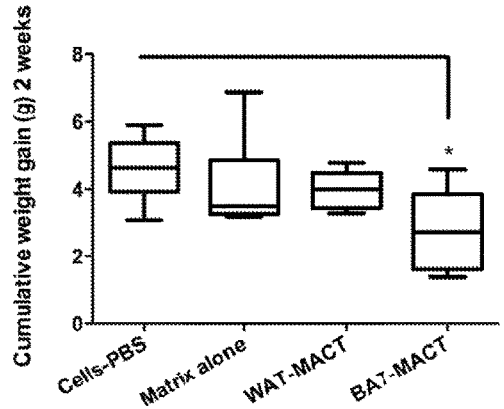
FIGS. 5A-F depict the effects of brown fat expansion on metabolic profiles.
Figure 5B:
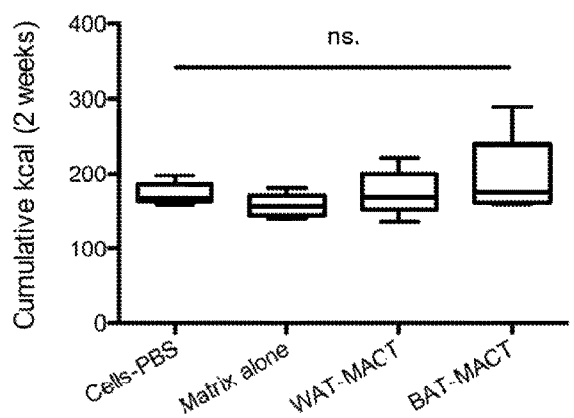
Figure 5C:
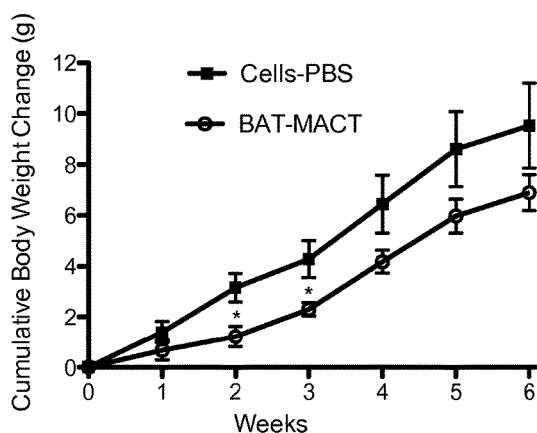
Figure 5D:
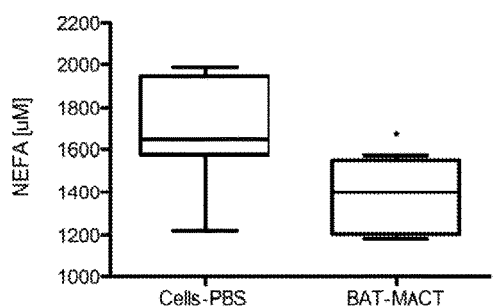
Figure 5E:
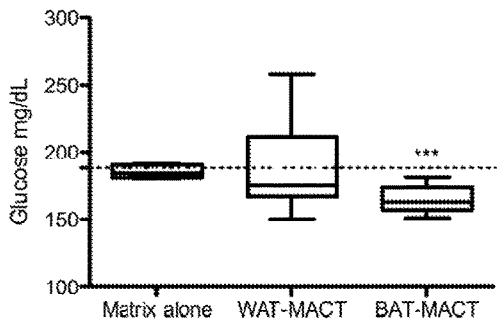
Figure 5F:
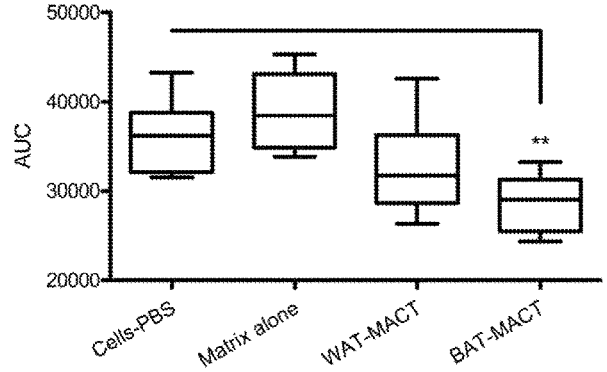

Using C57Bl/6 mice as a standard model for diet induced obesity, it was addressed if BAT-MACTs would have the expected impact on weight gain and glucose homeostasis Animals implanted with BAT-MACTs and housed at 21° C. gain significantly less weight when fed a 60% fat diet for 2 weeks (FIG. 5A) in spite of equal or slightly higher food consumption (FIG. 5B), while implantation of WAT-MACTs, BAT cells without matrix, or PBS injections did not significantly affect either parameter. A more detailed time course of weight changes showed that the reduction of weight gain was significant within 2 weeks post BAT-MACT implantation and concomitant high-fat feeding and was sustained over the time period coinciding with the peak BLI signal measured previously (FIG. 5C). After two weeks serum triglyceride levels were found to trend lower and serum free fatty acids were significantly reduced in animals augmented with BAT-MACTs (FIG. 5D). Accompanying the reduced weight gain and serum FFAs, it was also found that resting serum glucose levels (FIG. 5E) as well as glucose tolerance as assessed by GTT (FIG. 5F), were improved in BAT—but not WAT-MACTs, cell-free implants, or matrix free implants of BAT-like cells.

FIGS. 5A-F: Brown Fat expansion promotes improved metabolic profiles. A) Weight Gain of c57b16/j mice after two weeks of consuming 60% fat diet and being implanted with BAT-MACT or control (n=6). B) Kilocalories consumed by the animals in figure A over two weeks. C) Body weight of animals consuming a 60% fat diet over the course of 6 weeks (n=4). D) Serum Non-Esterified Fatty Acid concentration and E) resting blood glucose concentrations after 2 weeks of 60% fat diet. F) Glucose tolerance test area under curve (time points: 0, 20, 30, 60, and 120 minutes) with an identical dose of glucose given to animals after two weeks of consuming 60% fat diet and being implanted with BAT-MACT or control (n=6). E) Resting blood glucose 7 days after the initiation of 60% fat diet and implantation of BAT-MACT or control (n=6).

REFERENCES

1. Rosen, E. D. & Spiegelman, B. M. What we talk about when we talk about fat. *Cell* 156, 20-44 (2014).
2. Nicholls, D. G. & Locke, R. M. Thermogenic mechanisms in brown fat. *Physiol Rev* 64, 1-64 (1984).
3. Fedorenko, A., Lishko, P. V. & Kirichok, Y. Mechanism of fatty-acid-dependent UCP1 uncoupling in brown fat mitochondria. *Cell* 151, 400-413 (2012).
4. Cannon, B. & Nedergaard, J. Brown adipose tissue: function and physiological significance. *Physiol Rev* 84, 277-359 (2004).
5. Cypess, A. M. et al. Identification and importance of brown adipose tissue in adult humans. *N Engl J Med* 360, 1509-1517 (2009).
6. van Marken Lichtenbelt, W. D. et al. Cold-activated brown adipose tissue in healthy men. *N Engl J Med* 360, 1500-1508 (2009).
7. Virtanen, K. A. et al. Functional brown adipose tissue in healthy adults. *N Engl J Med* 360, 1518-1525 (2009).
8. Ma, S. W. & Foster, D. O. Uptake of glucose and release of fatty acids and glycerol by rat brown adipose tissue in vivo. *Can J Physiol Pharmacol* 64, 609-614 (1986).
9. Ouellet, V. et al. Outdoor temperature, age, sex, body mass index, and diabetic status determine the prevalence, mass, and glucose-uptake activity of 18F-FDG-detected BAT in humans. *The Journal of clinical endocrinology and metabolism* 96, 192-199 (2011).
10. Gunawardana, S. C. & Piston, D. W. Reversal of type 1 diabetes in mice by brown adipose tissue transplant. *Diabetes* 61, 674-682 (2012).
11. Stanford, K. I. et al. Brown adipose tissue regulates glucose homeostasis and insulin sensitivity. *J Clin Invest* 123, 215-223 (2013).
12. Himms-Hagen, J. et al. Effect of CL-316,243, a thermogenic beta 3-agonist, on energy balance and brown and white adipose tissues in rats. *Am J Physiol* 266, R1371-1382 (1994).
13. Ghorbani, M., Claus, T. H. & Himms-Hagen, J. Hypertrophy of brown adipocytes in brown and white adipose tissues and reversal of diet-induced obesity in rats treated with a beta3-adrenoceptor agonist. *Biochem Pharmacol* 54, 121-131 (1997).
14. Ohno, H., Shinoda, K., Spiegelman, B. M. & Kajimura, S. PPARgamma agonists induce a white-to-brown fat conversion through stabilization of PRDM16 protein. *Cell Metab* 15, 395-404 (2012).
15. Elabd, C. et al. Human multipotent adipose-derived stem cells differentiate into functional brown adipocytes. *Stem cells* 27, 2753-2760 (2009).
16. Schulz, T. J. et al. Identification of inducible brown adipocyte progenitors residing in skeletal muscle and white fat. *Proc Natl Acad Sci USA* 108, 143-148 (2011).
17. Ahfeldt, T. et al. Programming human pluripotent stem cells into white and brown adipocytes. *Nature cell biology* 14, 209-219 (2012).
18. Rodeheffer, M. S., Birsoy, K. & Friedman, J. M. Identification of white adipocyte progenitor cells in vivo. *Cell* 135, 240-249 (2008).
19. Nishio, M. et al. Production of functional classical brown adipocytes from human pluripotent stem cells using specific hemopoietin cocktail without gene transfer. *Cell Metab* 16, 394-406 (2012).
20. Kajimura, S. et al. Initiation of myoblast to brown fat switch by a PRDM16-C/EBP-beta transcriptional complex. *Nature* (2009).
21. Edelstein, M. L., Abedi, M. R., Wixon, J. & Edelstein, R. M. Gene therapy clinical trials worldwide 1989-2004—an overview. *The journal of gene medicine* 6, 597-602 (2004).
22. Ong, W. K. & Sugii, S. Adipose-derived stem cells: fatty potentials for therapy. *The international journal of biochemistry & cell biology* 45, 1083-1086 (2013).
23. Huang, S. J. et al. Adipose-derived stem cells: isolation, characterization, and differentiation potential. *Cell transplantation* 22, 701-709 (2013).
24. Griffith, L. G. & Swartz, M. A. Capturing complex 3D tissue physiology in vitro. *Nature reviews. Molecular cell biology* 7, 211-224 (2006).
25. Tseng, Y. H. et al. New role of bone morphogenetic protein 7 in brown adipogenesis and energy expenditure. *Nature* 454, 1000-1004 (2008).

26. Hoffman, M. P. et al. Cell type-specific differences in glycosaminoglycans modulate the biological activity of a heparin-binding peptide (RKRLQVQLSIRT) from the G domain of the laminin alpha1 chain. *J Biol Chem* 276, 22077-22085 (2001).
27. Nakahara, H. et al. A mechanism for regulation of melanoma invasion. Ligation of alpha6beta1 integrin by laminin G peptides. *J Biol Chem* 271, 27221-27224 (1996).
28. Nomizu, M. et al. Identification of cell binding sites in the laminin alpha 1 chain carboxyl-terminal globular domain by systematic screening of synthetic peptides. *J Biol Chem* 270, 20583-20590 (1995).
29. Ponce, M. L., Nomizu, M. & Kleinman, H. K. An angiogenic laminin site and its antagonist bind through the alpha(v)beta3 and alpha5beta1 integrins. *FASEB journal: official publication of the Federation of American Societies for Experimental Biology* 15, 1389-1397 (2001).
30. Engler, A. J., Sen, S., Sweeney, H. L. & Discher, D. E. Matrix elasticity directs stem cell lineage specification. *Cell* 126, 677-689 (2006).
31. Shapira-Schweitzer, K. & Seliktar, D. Matrix stiffness affects spontaneous contraction of cardiomyocytes cultured within a PEGylated fibrinogen biomaterial. *Acta biomaterialia* 3, 33-41 (2007).
32. Saha, K. et al. Substrate modulus directs neural stem cell behavior. *Biophysical journal* 95, 4426-4438 (2008).
33. Saha, K., Pollock, J. F., Schaffer, D. V. & Healy, K. E. Designing synthetic materials to control stem cell phenotype. *Curr Opin Chem Biol* 11, 381-387 (2007).
34. Heron-Milhavet, L. et al. Muscle-specific overexpression of CD36 reverses the insulin resistance and diabetes of MKR mice. *Endocrinology* 145, 4667-4676 (2004).
35. Kim, S., Chung, E. H., Gilbert, M. & Healy, K. E. Synthetic MMP-13 degradable ECMs based on poly(N-isopropylacrylamide-co-acrylic acid) semi-interpenetrating polymer networks. I. Degradation and cell migration. *Journal of biomedical materials research. Part A* 75, 73-88 (2005).
36. Chung, E. H. et al. Biomimetic artificial ECMs stimulate bone regeneration. *Journal of biomedical materials research. Part A* 79, 815-826 (2006).
37. Li, Y. J., Chung, E. H., Rodriguez, R. T., Firpo, M. T. & Healy, K. E. Hydrogels as artificial matrices for human embryonic stem cell self-renewal. *Journal of biomedical materials research. Part A* 79, 1-5 (2006).
38. Wall, S. T. et al. Multivalency of Sonic hedgehog conjugated to linear polymer chains modulates protein potency. *Bioconjug Chem* 19, 806-812 (2008).
39. Wall, S. T., Yeh, C. C., Tu, R. Y., Mann, M. J. & Healy, K. E. Biomimetic matrices for myocardial stabilization and stem cell transplantation. *Journal of biomedical materials research. Part A* 95, 1055-1066 (2010).
40. Mather, B. D., Viswanathan, K., Miller, K. M. & Long, T. E. Michael addition reactions in macromolecular design for emerging technologies. *Progress in Polymer Science* 31, 487-531 (2006).
41. Lutolf, M. P., Raeber, G. P., Zisch, A. H., Tirelli, N. & Hubbell, J. A. Cell-Responsive Synthetic Hydrogels. *Advanced materials* 15, 888-892 (2003).
42. Soloveva, V., Graves, R. A., Rasenick, M. M., Spiegelman, B. M. & Ross, S. R. Transgenic mice overexpressing the beta 1-adrenergic receptor in adipose tissue are resistant to obesity. *Molecular endocrinology* 11, 27-38 (1997).
43. Jimenez, M. et al. Beta 3-adrenoceptor knockout in C57BL/6J mice depresses the occurrence of brown adipocytes in white fat. *European journal of biochemistry/FEBS* 270, 699-705 (2003).
44. Gburcik, V., Cawthorn, W. P., Nedergaard, J., Timmons, J. A. & Cannon, B. An essential role for Tbx15 in the differentiation of brown and "brite" but not white adipocytes. *Am J Physiol Endocrinol Metab* 303, E1053-1060 (2012).
45. Hernandez, A., de Mena, R. M., Martin, E. & Obregon, M. J. Differences in the response of UCP1 mRNA to hormonal stimulation between rat and mouse primary cultures of brown adipocytes. *Cellular physiology and biochemistry: international journal of experimental cellular physiology, biochemistry, and pharmacology* 28, 969-980 (2011).
46. Ueta, C. B. et al. beta(1) Adrenergic receptor is key to cold- and diet-induced thermogenesis in mice. *The Journal of endocrinology* 214, 359-365 (2012).
47. Nguyen, K. D. et al. Alternatively activated macrophages produce catecholamines to sustain adaptive thermogenesis. *Nature* 480, 104-108 (2011).
48. Halbleib, M., Skurk, T., de Luca, C., von Heimburg, D. & Hauner, H. Tissue engineering of white adipose tissue using hyaluronic acid-based scaffolds. I: in vitro differentiation of human adipocyte precursor cells on scaffolds. *Biomaterials* 24, 3125-3132 (2003).
49. Stillaert, F. B. et al. Human clinical experience with adipose precursor cells seeded on hyaluronic acid-based spongy scaffolds. *Biomaterials* 29, 3953-3959 (2008).
50. Kim, E. H. & Heo, C. Y. Current applications of adipose-derived stem cells and their future perspectives. *World journal of stem cells* 6, 65-68 (2014).
51. Kim, Y. M. et al. Adipose-derived stem cell-containing hyaluronic acid/alginate hydrogel improves vocal fold wound healing. *The Laryngoscope* 124, E64-72 (2014).
52. Henkin, A. H. et al. Real time non-invasive imaging of fatty acid uptake in vivo. *ACS Chem Biol* (2012).
53. Wu, Q. et al. Fatty acid transport protein 1 is required for nonshivering thermogenesis in brown adipose tissue. *Diabetes* 55, 3229-3237 (2006).
54. Boss, O. & Farmer, S. R. Recruitment of brown adipose tissue as a therapy for obesity-associated diseases. *Frontiers in endocrinology* 3, 14 (2012).
55. Farmer, S. R. Obesity: Be cool, lose weight. *Nature* 458, 839-840 (2009).
56. Konno, M. et al. Adipose-derived mesenchymal stem cells and regenerative medicine. *Development, growth & differentiation* 55, 309-318 (2013).
57. Wu, J. et al. Beige adipocytes are a distinct type of thermogenic fat cell in mouse and human. *Cell* 150, 366-376 (2012).
58. O'Cearbhaill, E. D., Ng, K. S. & Karp, J. M. Emerging medical devices for minimally invasive cell therapy. *Mayo Clinic proceedings* 89, 259-273 (2014).
59. Chopra, A. et al. Augmentation of integrin-mediated mechanotransduction by hyaluronic acid. *Biomaterials* 35, 71-82 (2014).
60. Bellahcene, A. et al. Bone sialoprotein mediates human endothelial cell attachment and migration and promotes angiogenesis. *Circulation research* 86, 885-891 (2000).
61. Veron, D. et al. Acute podocyte vascular endothelial growth factor (VEGF-A) knockdown disrupts alphaV-beta3 integrin signaling in the glomerulus. *PLoS One* 7, e40589 (2012).

62. Fisher, F. M. et al. FGF21 regulates PGC-1alpha and browning of white adipose tissues in adaptive thermogenesis. *Genes Dev* 26, 271-281 (2012).
63. Rosenwald, M., Perdikari, A., Rulicke, T. & Wolfrum, C. Bi-directional interconversion of brite and white adipocytes. *Nature cell biology* 15, 659-667 (2013).
64. Jha, A. K. et al. Structural Analysis and Mechanical Characterization of Hyaluronic Acid-Based Doubly Cross-Linked Networks. *Macromolecules* 42, 537-546 (2009).
65. Rezania, A. & Healy, K. E. Biomimetic peptide surfaces that regulate adhesion, spreading, cytoskeletal organization, and mineralization of the matrix deposited by osteoblast-like cells. *Biotechnology progress* 15, 19-32 (1999).
66. Harbers, G. M., Gamble, L. J., Irwin, E. F., Castner, D. G. & Healy, K. E. Development and characterization of a high-throughput system for assessing cell-surface receptor-ligand engagement. *Langmuir: the ACS journal of surfaces and colloids* 21, 8374-8384 (2005).
67. Murayama, O., Nishida, H. & Sekiguchi, K. Novel peptide ligands for integrin alpha 6 beta 1 selected from a phage display library. *Journal of biochemistry* 120, 445-451 (1996).
68. Meng, Y. et al. Characterization of integrin engagement during defined human embryonic stem cell culture. *FASEB journal: official publication of the Federation of American Societies for Experimental Biology* 24, 1056-1065 (2010).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of increasing the number of brown adipocytes in an individual, the method comprising implanting into the individual a composition comprising:
   a) a hydrogel;
   b) a cell adhesion ligand embedded within the hydrogel, wherein the cell adhesion ligand enhances at least one of: (i) the differentiation of adipose derived mesenchymal stem cells (ADMSCs) into brown adipocytes; and (ii) the maintenance of brown adipocytes; and
   c) ADMSCs embedded within the hydrogel, wherein at least 10% of the ADMSCs differentiate into brown adipocytes, thereby increasing the number of brown adipocytes in the individual.

2. The method of claim 1, wherein said implanting provides for one or more of:
   a) reduction of blood glucose to within a normal range;
   b) increased insulin sensitivity;
   c) increased metabolic rate;
   d) weight loss; and
   e) supplementation of endogenous heat production.

3. The method of claim 1, wherein said implanting comprises injecting the composition into the individual prior to gelation of the hydrogel.

4. The method of claim 1, wherein the ADMSCs are autologous ADMSCs obtained from the individual.

5. The method of claim 1, wherein the cell adhesion ligand is a syndecan-1 ligand or an $\alpha_5\beta_{1/3}$ integrin ligand.

6. The method of claim 1, wherein the cell adhesion ligand comprises the amino acid sequence RKRLQVQLSIRT.

7. The method of claim 1, wherein the cell adhesion ligand comprises the amino acid sequence KAFDITYVRLKF.

8. The method of claim 1, wherein the cell adhesion ligand has a length of from about 10 amino acids to about 100 amino acids.

9. The method of claim 1, wherein the hydrogel comprises hyaluronic acid.

10. The method of claim 1, further comprising enhancing the differentiation of ADMSCs to into brown adipocytes or enhancing the maintenance of brown adipocytes with an enhancement compound.

11. The method of claim 1, wherein the hydrogel has a modulus in a range of from 5 pascals (Pa) to 500 kilopascals (kPa).

12. The method of claim 1, wherein the number of ADMSCs embedded within the hydrogel is in a range of from $1\times10^5$ to $1\times10^{10}$.

13. The method of claim 1, wherein the hydrogel comprises a factor release molecule and/or a cleavable cross-linker.

14. A method of inducing adipose derived mesenchymal stem cells (ADMSCs) to differentiate into brown adipocytes, the method comprising culturing ADMSCs with a composition under conditions and for a time period that provide for differentiation of at least 30% of the ADMSCs into brown adipocytes, wherein the composition comprises:
   a) a hydrogel; and
   b) a cell adhesion ligand embedded within the hydrogel, wherein the cell adhesion ligand enhances at least one of: (i) the differentiation of adipose derived mesenchymal stem cells (ADMSCs) into brown adipocytes; and (ii) the maintenance of brown adipocytes.

15. The method of claim 14, wherein said culturing occurs in vitro or in vivo.

16. The method of claim 14, wherein said method comprises, prior to culturing the ADMSCs with said composition, culturing the ADMSCs in the absence of the hydrogel in a first differentiation medium for a period of time in a range of from 6 hours to 7 days, in the presence of the cell adhesion ligand,
   wherein the first differentiation medium comprises at least one enhancement compound that enhances at least one of: (i) the differentiation of ADMSCs to into brown adipocytes; and (ii) the maintenance of brown adipocytes.

17. The method of claim 14, wherein the cell adhesion ligand is a syndecan-1 ligand or an $\alpha_5\beta_{1/3}$ integrin ligand.

18. The method of claim 14, wherein the cell adhesion ligand comprises the amino acid sequence RKRLQVQLSIRT.

19. The method of claim 14, wherein the cell adhesion ligand comprises the amino acid sequence KAFDITYVRLKF.

20. The method of claim 14, wherein the cell adhesion ligand has a length of from about 10 amino acids to about 100 amino acids.

21. The method of claim 14, wherein the hydrogel comprises hyaluronic acid.

22. The method of claim 14, wherein the hydrogel has a modulus in a range of from 5 pascals (Pa) to 500 kilopascals (kPa).

23. The method of claim 14, wherein the number of ADMSCs embedded within the hydrogel is in a range of from $1\times10^5$ to $1\times10^{10}$.

24. The method of claim 14, wherein the hydrogel comprises a factor release molecule and/or a cleavable cross-linker.

25. The method of claim 16, wherein the enhancement compound is selected from the group consisting of: vascular endothelial growth factor (VEGF), bone morphogetnic protein 7 (BMP7), sonic hedgehog (SHH), brain natriuretic peptide (BNP), brain-derived neurotrophic factor (BDNF), fibroblast growth factor 21 (FGF21), transforming growth factor, beta (TGFβ), wingless-type MMTV integration site family, member 10B (Wnt10b), 1-methyl-3-isobutylxanthine (IBMX), insulin, 3,3',5 Triiodothyronine (T3), dexamethasone, rosiglitazone, and a combination thereof.

26. A method of increasing the number of brown adipocytes in an individual, the method comprising:
   (a) culturing adipose derived mesenchymal stem cells (ADMSCs) in the absence of a hydrogel in a first differentiation medium for a period of time in a range of from 6 hours to 7 days, in the presence of a cell adhesion ligand, wherein the first differentiation medium comprises at least one enhancement compound that enhances at least one of: (i) the differentiation of ADMSCs to into brown adipocytes; and (ii) the maintenance of brown adipocytes, thereby producing a population of primed ADMSCs;
   (b) mixing cells of the population of primed ADMSCs with a composition that includes a hydrogel and a cell adhesion ligand that enhances at least one of: (i) the differentiation of adipose derived mesenchymal stem cells (ADMSCs) into brown adipocytes; and (ii) the maintenance of brown adipocytes, thereby producing a cell-loaded loaded hydrogel; and
   (c) implanting the cell-loaded hydrogel into the individual.

* * * * *